United States Patent
Baine et al.

(10) Patent No.: US 11,883,478 B2
(45) Date of Patent: Jan. 30, 2024

(54) METHOD OF TREATMENT

(71) Applicant: GLAXOSMITHKLINE BIOLOGICALS S.A., Rixensart (BE)

(72) Inventors: Yaela Baine, Philadelphia, PA (US); Jacqueline Miller, Philadelphia, PA (US)

(73) Assignee: GLAXOSMITHKLINE BIOLOGICALS S.A., Rixensart (BE)

(*) Notice: Subject to any disclaimer, the term of this patent is extended or adjusted under 35 U.S.C. 154(b) by 0 days.

(21) Appl. No.: 14/777,985

(22) PCT Filed: Mar. 17, 2014

(86) PCT No.: PCT/EP2014/055355
§ 371 (c)(1),
(2) Date: Sep. 17, 2015

(87) PCT Pub. No.: WO2014/147044
PCT Pub. Date: Sep. 25, 2014

(65) Prior Publication Data
US 2016/0279225 A1 Sep. 29, 2016

Related U.S. Application Data

(60) Provisional application No. 61/874,008, filed on Sep. 5, 2013, provisional application No. 61/802,918, filed on Mar. 18, 2013.

(51) Int. Cl.
*A61K 39/095* (2006.01)
*A61K 39/102* (2006.01)
*A61K 39/00* (2006.01)

(52) U.S. Cl.
CPC .......... *A61K 39/095* (2013.01); *A61K 39/102* (2013.01); *A61K 2039/55* (2013.01); *A61K 2039/6037* (2013.01); *A61K 2039/70* (2013.01); *Y02A 50/30* (2018.01)

(58) Field of Classification Search
CPC ................. A61K 39/095; A61K 39/102; A61K 2039/55; A61K 2039/70; A61K 2039/6037
See application file for complete search history.

(56) References Cited

U.S. PATENT DOCUMENTS

| | | | | |
|---|---|---|---|---|
| 2003/0068336 A1* | 4/2003 | Ryall | ............ | A61K 39/095 424/250.1 |
| 2008/0193476 A1* | 8/2008 | Biemans | ............ | A61K 39/095 424/197.11 |
| 2008/0254057 A1* | 10/2008 | Costantino | ............ | A61K 47/646 424/197.11 |
| 2008/0305127 A1* | 12/2008 | Poolman | ............ | A61K 39/092 424/194.1 |
| 2009/0041802 A1* | 2/2009 | Biemans | ............ | A61K 39/0017 424/197.11 |

FOREIGN PATENT DOCUMENTS

| | | |
|---|---|---|
| AU | 2012/203419 | 7/2012 |
| WO | 99/42130 A1 | 8/1999 |
| WO | 2007000314 A2 | 1/2007 |
| WO | 2007/111940 A2 | 10/2007 |
| WO | WO-2007111940 A2 * | 10/2007 ........... A61K 39/095 |

OTHER PUBLICATIONS

Pichichero 2005 (Meningococcal Conjugate Vaccine in Adolescents and Children; Clinical Pediatrics, July/August, 479-489).*
Croxtall et al. 2012 (Meningococcal Quadrivalent (Serogroups A, C, W135 and Y) Tetanus Toxoid Conjugate Vaccine (NimenrixTM); Drugs 72(18):2407-2430 (Year: 2012).*
Brady et al. 2011 (Meningococcal conjugate vaccines policy update: booster dose recommendations; Pediatrics 128(6): 1213-1218 (Year: 2011).*
Findlow et al. 2013 (Immunogenicity and Safety of a Meningococcal Serogroup A, C, Y, and W Glycoconjugate Vaccine, ACWY-TT; Adv. Ther. 30:431-458). (Year: 2013).*
Olander et al. 2002 (Booster response to the tetanus and diphtheria toxoid carriers of 11-valent pneumococcal conjugate vaccine in adults and toddlers; Vaccine 20: 336-341) (Year: 2002).*
Schmitt, et al., Immunogenicity, Reactogenicity, and Immune Memory after Primary Vaccination with a Novel Haemophilus influenzae-Neisseria meningitidis Serogroup C Conjugate Vaccine, Clinical and Vaccine Immunology 14(4):426-434 (2007).
Gatchalian, et al., The development of a new heptavalent diphtheria-tetanus-whole cell pertussis-hepatitis B-Haemophilus influenzae type b-Neisseria meningitidis serogroups A and C vaccine: a randomized dose-ranging trial of the conjugate vaccine components, International Journal of Infectious Diseases 12(3):278-288 (2008).
Borrow, et al., Kinetics of Antibody Persistence following Administration of a Combination Meningococcal Serogroup C and Haemophilus influenzae Type b Conjugate Vaccine in Healthy Infants in the United Kingdom Primed with a Monovalent Meningococcal Serogroup C Vaccine, Clinical and Vaccine Immunology 17(1):154-159 (2010).

(Continued)

*Primary Examiner* — Gary B Nickol
*Assistant Examiner* — Amelia Nicole Dickens
(74) *Attorney, Agent, or Firm* — Seed IP Law Group LLP

(57) ABSTRACT

The application discloses method of immunising against *Neisseria meningitidis* infection comprising the steps of a) immunising a human patient at a first age of between 0 and 11 months with a bacterial saccharide conjugate vaccine comprising at least one, two or three bacterial saccharide(s) separately conjugated to a carrier protein to form at least one, two or three bacterial saccharide conjugate(s); and b) immunising the human patient at a second age of between 12 and 24 months with a *Neisseria meningitidis* conjugate vaccine comprising at least two capsular saccharides selected from the group consisting of *N. meningitidis* serogroup A capsular saccharide (MenA), *N. meningitidis* serogroup C capsular saccharide (MenC), *N. meningitidis* serogroup W135 capsular saccharide (MenW135), and *N. meningitidis* serogroup Y capsular saccharide (MenY) conjugated separately to a carrier protein, wherein the *Neisseria meningitidis* conjugate vaccine is co-administered with a vaccine comprising diphtheria toxoid and tetanus toxoid.

40 Claims, 4 Drawing Sheets

(56) References Cited

OTHER PUBLICATIONS

Gasparini, et al., Meningococcal glycoconjugate vaccines, Human Vaccines 7(2):170-182 (2011).

Nolan, et al., Immunogenicity and Safety of an Investigational Combined Haemophilus influenzae Type B-Neisseria meningitidis Serogroups C and Y-Tetanus Toxoid Conjugate Vaccine, Pediatric Infectious Disease Journal 30(3):190-196 (2011).

Habermehl et al., "Combined Haemophilus influenzae type b and Neisseria meningitidis serogroup C (HibMenC) or serogroup C and Y-tetanus toxoid conjugate (and HibMenCY) vaccines are well-tolerated and immunogenic when administered according to the 2,3,4 months schedule with a fourth dose at 12-18 months of age," Human Vaccines 6(8):640-651, DOI: 10.4161/hv.6.8.12154 (Aug. 1, 2010).

Knuf et al., "An investigational tetravalent meningococcal serogroups A, C, W-135 and Y-tetanus toxoid conjugate vaccine co-administered with Infranix™ hexa is immunogenic, with an acceptable safety profile in 12-23-month-old children," Vaccine 29:4264-4273 (2011).

Marshall et al., "Co-administration of a novel Haemophilus influenzae type b and Neisseria meningitidis serogroups C and Y-tetanus toxoid conjugate vaccine does not interfere with the immune response to antigens contained in infant vaccines routinely used in the United States," Human Vaccines 7(2):258-264, DOI: 10.4161/hv.7.2.14170 (Feb. 1, 2011).

Vesikari et al., "Randomized trial to assess the immunogenicity, safety and antibody persistence up to three years after a single dose of a tetravalent meningococcal serogroups A, C, W-135 and Y tetanus toxoid conjugate vaccine in toddlers," Human Vaccines & Immunotherapeutics 8(12): 1892-1903, DOI: 10.4161/hv.22166 (Oct. 2, 2012).

Frasch et al. "Development of a group A meningococcal conjugate vaccine, MenAfriVac™," Human Vaccines & Immunotherapeutics 8(6):715-724, DOI: 10.4161/hv.19619, 2012.

"Infant Meningococcal Vaccination: Advisory Committee on Immunization Practices (ACIP) Recommendations and Rationale," Morbidity and Mortality Weekly Report (MMWR) 62(03):52-54, 2013.

"Recommendation of the Advisory Committee on Immunization Practices (ACIP) for Use of Quadrivalent Meningococcal Conjugate Vaccine (MenACWY-D) Among Children Aged 9 Through 23 Months at Increased Risk for Invasive Meningococcal Disease," Morbility and Mortality Weekly Report (MMWR) 60(40):1391-1392, 2011.

Takahashi et al., "Induction of CD8+ cytotoxic T cells by immunization with purified HIV-1 envelope protein in ISCOMs," Nature 344:873-875, 1990.

Vaccine Design: The Subunit and Adjuvant Approach, Pharmaceutical Biotechnology, vol. 6, edited by Michael F. Powell et al., Springer Science+Business Media New York 1995, 997 pages.

Schutze et al, "Carrier-induced epitopic suppression, a major issue for future synthetic vaccines," The Journal of Immunology, 135(4): 2319-2322, 1985.

Dagan et al., "Glycoconjugate vaccines and immune interference: A review," Elsevier, Vaccine28:5513-5523, 2010.

Bryant et al, "Immunogenicity and Safety of H influenza Type b-N meningitides C/Y Conjugate Vaccine in Infants," Pediatrics [frequently abbreviated] 127(6): e1375-e1385 2011.

Marshall et al, "Immune Response and One-Year Antibody Persistence After a Fourth Dose of a Novel Haemophilus Influenzae Type B and Neisseria Meningitidus Serogroups C and Y-Tetanus Toxoid Conjugate Vaccine (H18MenCY) at 12 to 15 Months of Age," The Pediatric Infectious Disease Journal 29(5): 469-471, 2010.

Response to Opponent's Submissions dated Feb. 23, 2022, European Patent Application No. 14711232.0, 3 pages.

Opponent's Response dated Mar. 3, 2022, European Patent Application No. 14711232.0, 2 pages.

Clinicaltrials.gov, D36 filed with Opponent's Response dated Mar. 3, 2022, European Patent Application No. 14711232.0, 4 pages.

Email from ClinicalTrial.gov Registration, D37 filed with Opponent's Response dated Mar. 3, 2022, European Patent Application No. 14711232.0, 2 pages.

"Advisory Committee on Immunization Practice (ACIP) Votes to Recommend Routine Use of Combined Tetanus, Diphtheria and Pertussis (Tdap) Vaccines for Adolescents," Archive Capture of CDC Webpage dated Oct. 29, 2005, 2 pages.

"History of Changes for Study: NCT00614614" ClinicalTrials.gov archive, URL: https://www/clinicaltrials.gov/ct2/history/NCT00614614?V_16=View#StudyPageTop, Jul. 20, 2012, 33 pages.

"History of Changes for Study: NCT00614614" ClinicalTrials.gov archive, URL: https://www/clinicaltrials.gov/ct2/history/NCT00614614?V_17=View#StudyPageTop, Nov. 23, 2011, 7 pages.

"History of Changes for Study: NCT00614614" ClinicalTrials.gov archive, URL: https://www/clinicaltrials.gov/ct2/history/NCT00614614?V_19=View, Aug. 30, 2012, 67 pages.

"History of Changes for Study: NCT00667602" ClinicalTrials.gov archive, URL: https://www/clinicaltrials.gov/ct2/history/NCT00667602?V_12=View#StudyPageTop, Nov. 7, 2013, 49 pages.

"History of Changes for Study: NCT01659996" ClinicalTrials.gov archive, URL: https://www/clinicaltrials.gov/ct2/history/NCT01659996?A=2&B=2&C=merged#StudyPageTop, Feb. 6, 2013, 6 pages.

Dagan et al., "Reduced Response to Multiple Vaccines Sharing Common Protein Epitopes That Are Administered Simultaneously to Infants," Infection and Immunity 66(5):2093-2098, 1998.

"European Commission, Commission Implementing Decision of Apr. 20, 2012, granting marketing authorization under Regulation (EC) No. 726/2004 of the European Parliament and of the Council for "Nimenrix—Meningococcal Group A, C, W-135 and Y conjugate vaccine," a medicinal product for human use," Brussels, Apr. 20, 2012, 58 pages.

European Commission, Commission Decision of Aug. 31, 2010, on the renewal of the marketing authorisation for the medicinal product for human use "Infanrix hexa—Diphtheria, tetanus, acellular pertussis, hepatitis B recombinant (adsorbed), inactivated poliomyelitis and adsorbed conjugated Haemophilus influenzae type b vaccine," granted by Decision C(2000)2848, Brussels, Aug. 31, 2010, 72 pages.

Gasparini et al., "Meningococcal glycoconjugate vaccines," Human Vaccines 7:2, 170-182, Feb. 2011.

"Glossary of Common Site Terms," ClinicalTrials.gov, URL: https://clinicaltrials.gov/ct2/about-studies/glossary, Dec. 2020, 19 pages.

"Result Summaries: Meningococcal Serogroups A, C, W-135 and Y-Tetanus Toxoid Conjugate Vaccine," Archive Capture of GSK Webpage, May 27, 2012.

"Meningococcal Groups C and Y and Haemophilus b Tetanus Toxoid Conjugate Vaccine," Archive Capture of FDA Webpage, Jun. 22, 2012.

"Recommended Childhood and Adolescent Immunisation Schedule—United States 2005," Morbidity and Mortality Weekly Report (MMWR) dated Jan. 7, 2005, 3 pages.

Immuno, Safety of GSK Vaccine 134612 Given at Age of 12-15 Months 15-18 Months Post-priming With GSK Vaccine 792014, ClinicalTrials.gov Identifier: NCT00614614, ClinicalTrials.gov, URL: https://clinicaltrials.gov/ct2/show/NCT00614614, Sep. 21, 2018, 14 pages.

Response to Opposition, European Patent No. EP 2 976 101 B1, Glaxo SmithKline Biologicals S.A., Opponent: Sanofi Pasteur S.A., Oct. 13, 2021, 48 pages.

"Infanrix® Diphtheria and Tetanus Toxoids and Acellular Pertussis Vaccine Adsorbed," Jul. 2003, 26 pages.

Menactra®, Highlights of Prescribing Information, Sanofi Pasteur, Nov. 30, 2011, 36 pages.

Menhibrix®, Highlights of Prescribing Information, GSK, 2012, 14 pages.

Menveo®, Highlights of Prescribing Information, Novartis Vaccines and Diagnostics S.r.l., 2010, 16 pages.

Opposition Response for EP 14711232.0, dated Dec. 22, 2021, 4 pages.

Pediarix™ (Diphtheria and Tetanus Toxoids and Acellular Pertussis Adsorbed, Hepatitis B (Recombinant) and Inactivated Poliovirus Vaccine Combined), SmithKline Beecham Biologicals, Dec. 2002, 26 pages.

(56) References Cited

OTHER PUBLICATIONS

PCT Request, PCT/EP2014/055355, filed Mar. 17, 2014, 5 pages.
"Sanofi Pasteur announces FDA approval of Menactra®," Sanofi Pasteur, URL: https://www.europeanpharmaceuticalreview.com/news/6917/sanofi-pasteur-announces-fda-approval-of-menactra/, Apr. 22, 2011, 4 pages.
"GSK receives FDA approval for MenHibrix," GlaxoSmithKline, URL: https://www.europeanpharmaceuticalreview.com/news/13303/gsk-receives-fda-approval-menhibrix/, Jun. 14, 2012, 5 pages.
"SmithKline receives European authorization for Nimenrix™," GlaxoSmithKline, URL: https://www.european pharmaceuticalreview.com/news/12515/glaxosmithkline-receives-european-authorisation-for-nimenrix/, Apr. 27, 2012, 4 pages.
Pöllabauer et al., "The influence of carrier protein on the immunogenicity of simultaneously administered conjugate vaccines in infants," *Vaccine* 27:1674-1679, Jan. 2009.
Snape et al., "Immunogenicity of a Tetravalent Meningococcal Glycoconjugate Vaccine in Infants. A Randomized Controlled Trial," *JAMA* 299(2): 173-184, Jan. 2008.
Vesikari et al., "Tetravalent meningococcal serogroups A, C, W-135 and Y conjugate vaccine is well tolerated and immunogenic when co-administered with measles-mumps-rubella-varicella vaccine during the second year of life: An open, randomized controlled trial," *Vaccine* 29:4274-4284, Apr. 2011.
Opposition Statement, European Patent No. EP2976101, Sanofi Pasteur S.A., May 18, 2021, 21 pages.
Decker et al., 40—Combination vaccines, Editor(s): Stanley A. Plotkin, Walter A. Orenstein, Paul A. Offit, *Vaccines* (Sixth Edition), W.B. Saunders, 2013, pp. 981-1007, ISBN 9781455700905.
Granoff et al., 21—Meningococcal vaccines, Editor(s): Stanley A. Plotkin, Walter A. Orenstein, Paul A. Offit, *Vaccines* (Sixth Edition), W.B. Saunders, 2013, pp. 388-418, ISBN 9781455700905.
Anonymous, "Product Summary," MENJUGATE (Meningococcal C-CRM 197 Conjugate Vaccine), revised Feb. 2000. (7 pages).
Bröker et al., "Chemistry of a new investigational quadrivalent meningococcal conjugate vaccine that is immunogenic at all ages," *Vaccine* 27:5574-5580, Jul. 2009. (7 pages).
EMC, "Summary of Product Characteristics," Menitorix—Powder and solvent for solution for injection; Haemophilus type b and Meningococcal group C conjugate vaccine, last updated Jun. 3, 2009. (8 pages).
Esposito et al., "Differences in vaccinations in European Union," Human Vaccines 4(4):313- 315, Jul./Aug. 2008. (3 pages).
European Medicines Agency, "European Public Assessment Report; Nimenrix," Meningococcal group A, C, W-135 and Y conjugate vaccine, Procedure No. EMEA/H/C/002226, May 24, 2012. (85 pages).
Knuf et al., "A dose-range study assessing immunogenicity and safety of one dose of a new candidate meningococcal serogroups A, C, W-135, Y tetanus toxoid conjugate (MenACWY-TT) vaccine administered in the second year of life and in young children," *Vaccine* 28:744-753, Nov. 2009. (10 pages).
NHS, "Factsheet: Haemophilus influenzae type b (Hib) and meningococcal serogroup C (MenC) vaccines for children," COI for the Department of Health, Aug. 2006. (20 pages).
NHS, "Routine childhood immunisations from Nov. 2010," Immunisation Information, 2010. (1 page).
Opponent's Written Submissions, dated Jul. 27, 2023, for European Patent No. 2976101. (19 pages).
Opponent's Written Submissions, dated Sep. 14, 2023, for European Patent No. 2976101. (3 pages).
Patentee's Written Submissions, dated Jul. 26, 2023, for European Patent No. 2976101. (7 pages).
Patentee's Written Submissions, dated Sep. 20, 2023, for European Patent No. 2976101. (1 page).
Trotter et al., "A surveillance network for meningococcal disease in Europe," *FEMS Microbiology Reviews* 31:27-36, 2007 [Published Online Dec. 2006] (10 pages).
Vliegenthart, "Minireview: Carbohydrate based vaccines," *FEBS Letters* 580:2945-2950, Mar. 2006. (6 pages).
Wikipedia, "Hexavalent vaccine," URL=https://en.wikipedia.org/wiki/Hexavalent_vaccine, download date May 23, 2023. (2 pages).
Wikipedia, "Adipic acid dihydrazide," URL=https://en.wikipedia.org/w/index.php?title=Adipic_acid_dihydrazide&oldid=465861182, download date Sep. 6, 2023. (2 pages).

* cited by examiner

METHOD OF TREATMENT

This application is filed pursuant to 35 U.S.C. § 371 as a United States National Phase Application of International Patent Application Serial No. PCT/EP2014/055355 filed Mar. 17, 2014, which claims priority to U.S. Provisional Application No. 61/874,008 filed Sep. 5, 2013 and to U.S. Provisional Application No. 61/802,918 filed Mar. 18, 2013, and the entire contents of each of the foregoing applications are hereby incorporated by reference.

TECHNICAL FIELD

The present invention relates to the field of uses of conjugate vaccines against *Neisseria meningitidis* for the prevention or treatment of *N. meningitidis* infection. In particular, the present invention relates to the coadministration of *N. meningitidis* conjugate vaccines with vaccines containing DTP in a population which has been preimmunised with at least one conjugate vaccine. A further aspect of the invention relates to the use of a further immunisation

BACKGROUND

Invasive *Neisseria meningitidis* infection causes severe disease with approximately 10% mortality even when appropriate antibiotics and supportive therapy are administered [1]. In the United States the majority of invasive meningococcal disease (IMD) is caused by serogroups B, C and Y [2], while serogroups A, W-135 and X, which are important causes of disease outbreaks in many regions worldwide [3,4] are more rarely detected. Infants younger than 1 year of age have the highest incidence of IMD in the US (approximately 1:18,500 population; 1998-2007) [2]. Therefore, in order to impact meningococcal disease in US infants and children, meningococcal conjugate vaccines need to be effective from early ages [5].

The meningococcal serogroup C and Y vaccine, combined with Hib (HibMenCY-TT, MenHibrix™, GlaxoSmithKline Vaccines), was recently licensed in the US for use in infants as a 4-dose series beginning at 2 months of age [6], after demonstration of immunogenicity and safety in clinical trials conducted in infants and toddlers [7-14]. One quadrivalent serogroups A, C, W-135 and Y (MenACWY) meningococcal conjugate vaccine is licensed in the US for use in children aged 9-12 months (Menactra™, sanofi pasteur): two doses of which are recommended by the Advisory Committee on Immunization Practices (ACIP) for children at increased risk for IMD due to complement deficiency or exposure due to travel/residence in an endemic area [15]. Another MenACWY conjugate vaccine is licensed for use from 2 years of age (Menveo™, Novartis).

GlaxoSmithKline Vaccines' MenACWY vaccine with all serogroups conjugated to tetanus toxoid (TT) (MenACWY-TT: Nimenrix™), is licensed as a single dose in Europe, but remains investigational in the US. Clinical trials have demonstrated that one dose of MenACWY-TT is immunogenic for all four serogroups and well tolerated in toddlers from 12 months of age, children, adolescents and adults [16-23].

The paediatric immunisation schedule is crowded and there remains a need to evaluate the safety and immunogenicity of meningococcal conjugate vaccines when introduced into an immunisation schedule with the paediatric vaccines. It is valuable to establish whether coadministration with other vaccines leads to interference problems or enhanced immunogenicity.

The present study evaluates the immunogenicity and safety of meningococcal conjugate vaccines when administered as a further dose in the second year of life. In particular, it reports on the effect of co-administering with a dose of diphtheria-tetanus-acellular (DTPa) vaccine during the second year of life.

The study has unexpectedly shown that co-administration of a multivalent meningococcal conjugate vaccine with DTPa containing vaccines in the second year of life leads to an enhanced immune response against the meningococcal conjugates compared to when the vaccines are administered at different time points. A simpler immunisation schedule in which meningococcal conjugate and DTPa are co-administered leads to the double benefit of fewer visits to a clinic and improved immunogenicity.

Accordingly to one aspect of the invention, there is provided a method of immunising against *Neisseria meningitidis* infection comprising the steps of a) immunising a human patient at a first age of between 0 and 11 months with at least one bacterial saccharide conjugated to a first carrier protein to form a bacterial saccharide conjugate; and b) immunising the human patient at a second age of between 12 and 24 months with a *Neisseria meningitidis* conjugate vaccine comprising at least two capsular saccharides selected from the group consisting of *N. meningitidis* serogroup A capsular saccharide (MenA), *N. meningitidis* serogroup A capsular saccharide *N. meningitidis* serogroup C capsular saccharide (MenC), *N. meningitidis* serogroup W135 capsular saccharide (MenW135), and *N. meningitidis* serogroup Y capsular saccharide (MenY) conjugated separately to a second carrier protein, wherein the *Neisseria meningitidis* conjugate vaccine is co-administered with a vaccine comprising diphtheria toxoid and tetanus toxoid.

According to a further aspect of the invention, there is provided a medical use of a multivalent *N. meningitidis* conjugate vaccine in the prevention or treatment of *N. meningitidis* disease wherein a human patient is immunised in a schedule comprising steps a) and b) wherein step a) immunises a human patient at a first age of between 0 and 11 months with at least one bacterial saccharide conjugated to a first carrier protein to form a bacterial saccharide conjugate; and step b) immunises the human patient at a second age of between 12 and 24 months with a *Neisseria meningitidis* conjugate vaccine comprising at least two capsular saccharides selected from the group consisting of *N. meningitidis* serogroup A capsular saccharide (MenA), *N. meningitidis* serogroup A capsular saccharide *N. meningitidis* serogroup C capsular saccharide (MenC), *N. meningitidis* serogroup W135 capsular saccharide (MenW135), and *N. meningitidis* serogroup Y capsular saccharide (MenY) conjugated separately to a second carrier protein, wherein the *Neisseria meningitidis* conjugate vaccine is co-administered with a vaccine comprising diphtheria toxoid and tetanus toxoid.

See Supplemental table 3 for details of the reasons why subjects withdrew from the study or were eliminated from the According to Protocol immunogenicity cohort during the Fourth dose phase \* subjects did not participate in the Fourth dose Phase because they were unwilling to participate (n=83); were lost to follow up (n=47); or were not eligible to participate (n=78).

Figure 2:
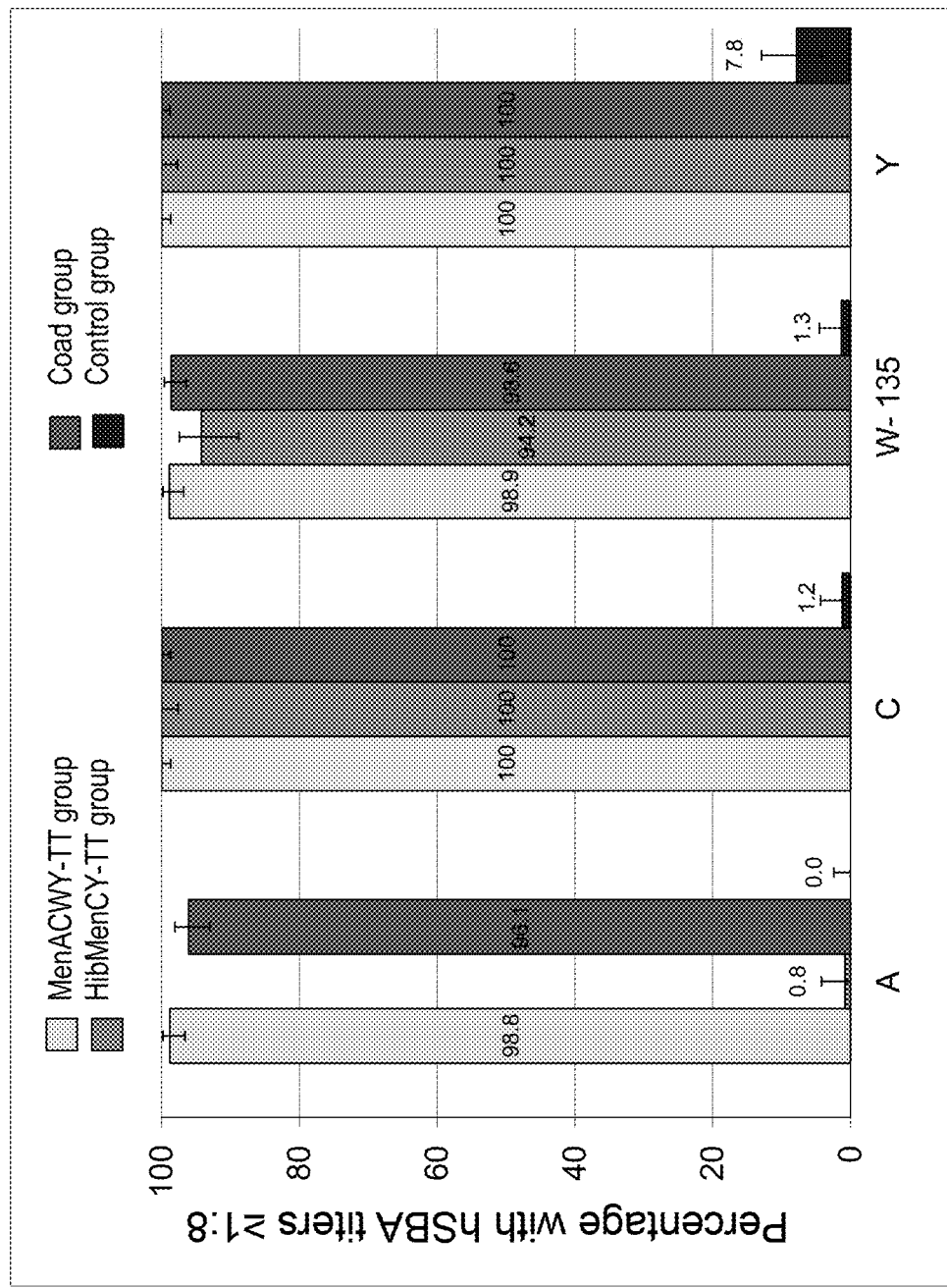

FIG. 2: Percentage of subjects with hSBA titers 1:8 one month after vaccination with MenACWY-TT or HibMenCY-TT at 12-15 months of age, with MenACWY-TT+DTaP at 15-18 months of age or with DTaP at 15-18 months of age (Control group) (ATP immunogenicity cohort, Fourth Dose Phase).

Figure 3:
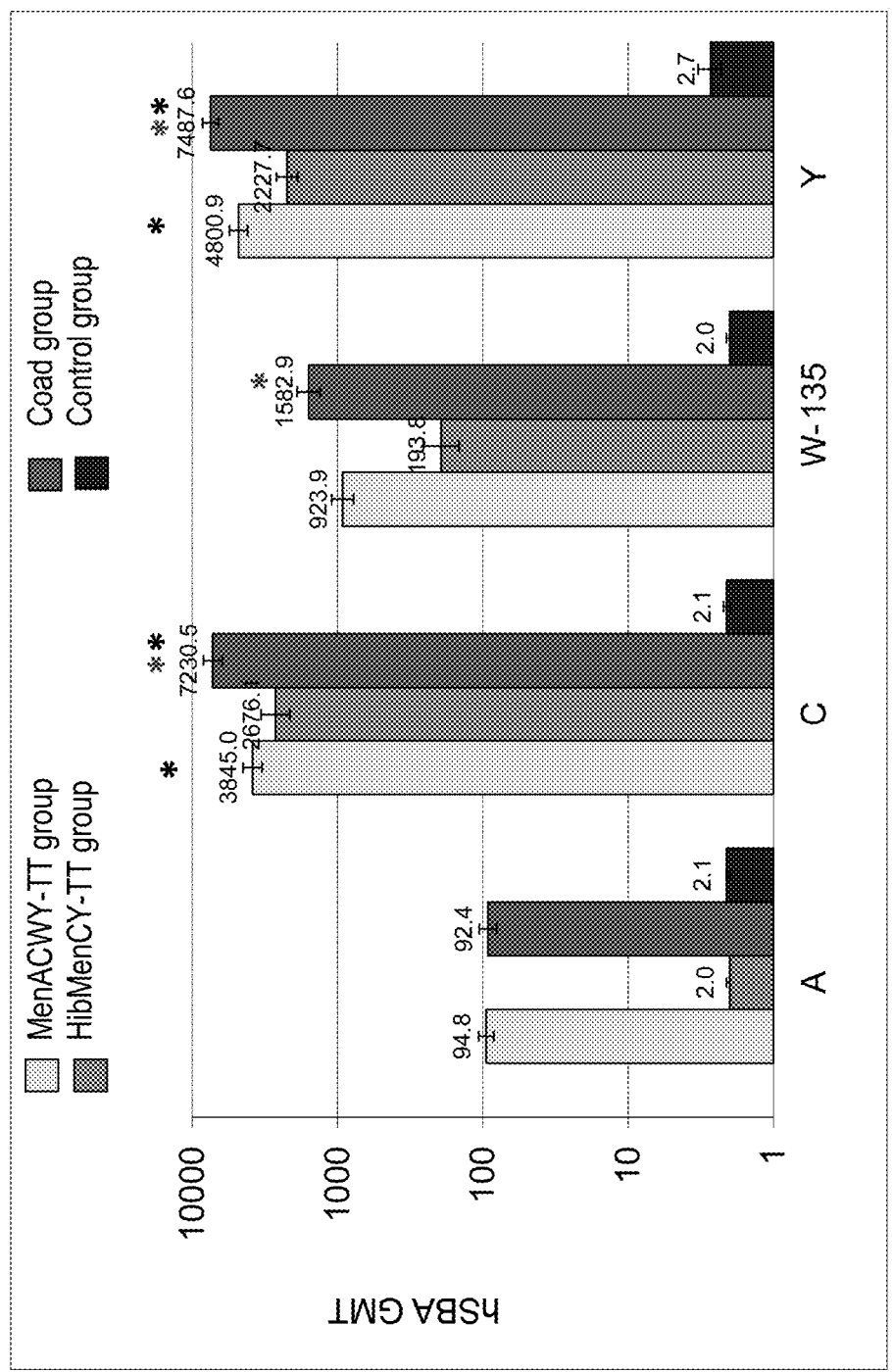

ATP=According to protocol; hSBA=serum bactericidal activity using human complement source FIG. 3: hSBA GMTs one month after vaccination with MenACWY-TT or HibMenCY-TT at 12-15 months of age, or with MenACWY-TT+DTaP at 15-18 months of age or with DTaP at 15-18 months of age (Control group) (ATP immunogenicity cohort, Fourth Dose Phase).

ATP=According to protocol; hSBA=serum bactericidal activity using human complement source; GMT=geometric mean titer

* Represents differences observed between the coadminstration group and other groups.

Figure 4:
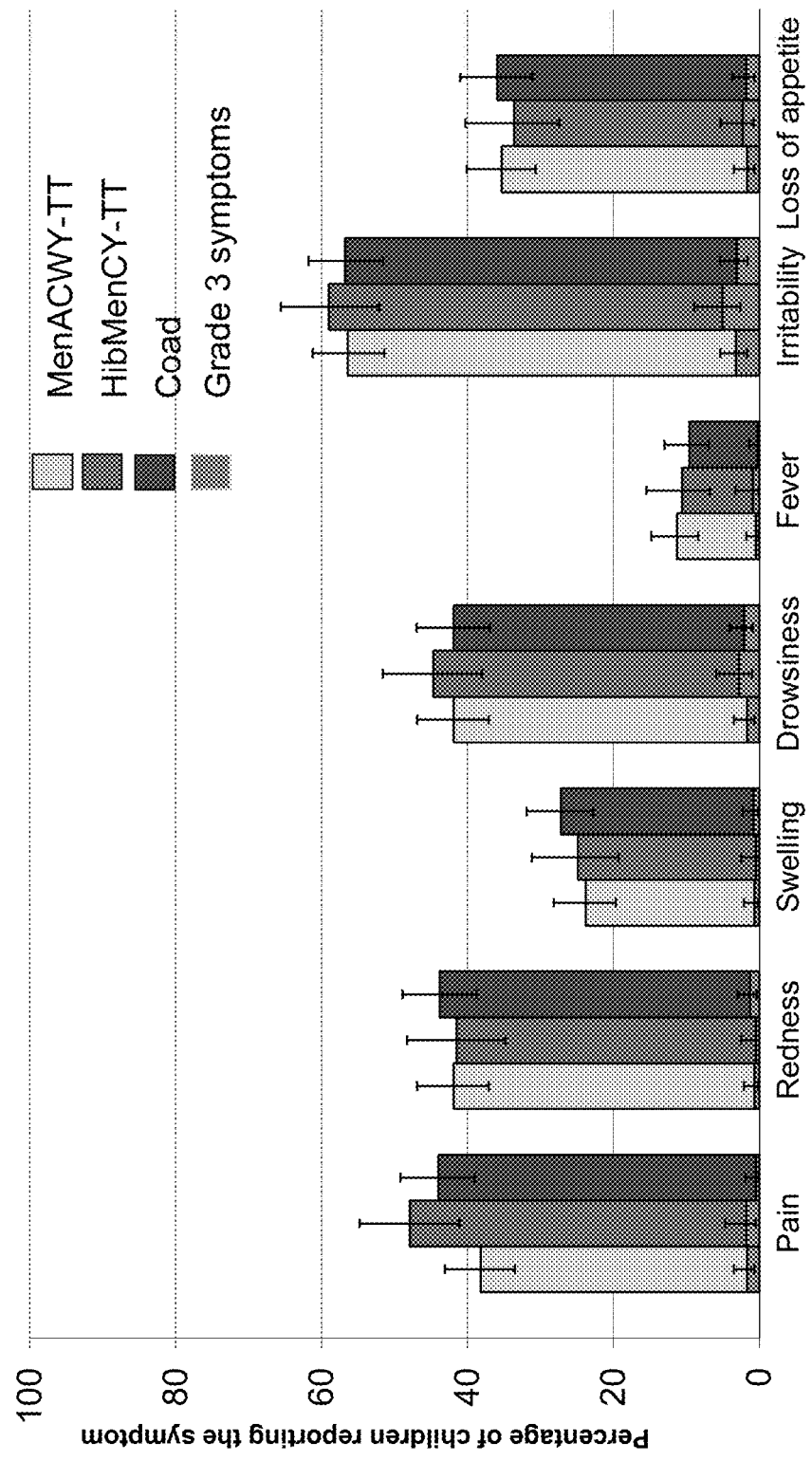

FIG. 4: Local and general solicited symptoms within 8 days after vaccination with MenACWY-TT or HibMenCY-TT at 12-15 months of age, or of DTaP and MenACWY-TT (Coad group) at 15-18 months of age (Total vaccinated cohort, Fourth Dose Phase).

For all groups, local symptoms refer to the percentage of subjects with at least one local symptom at the MenACWY-TT or HibMenCY-TT injection site. Any fever (any route)≥38.0° C.; Grade 3: Redness and swelling>30 mm; Pain—cried when limb was touched/spontaneously painful; Fever (any route)>40° C.; Irritability/Fussiness and Drowsiness—prevented normal activity; Loss of appetite—not eating at all.

DETAILED DESCRIPTION

The present invention discloses a method of immunising against *Neisseria meningitidis* infection comprising the steps of a) immunising a human patient at a first age of between 0 and 11 months with at least one bacterial capsular saccharide conjugated to a first carrier protein to form a bacterial capsular saccharide conjugate; and b) immunising the human patient at a second age of between 12 and 24 months with a *Neisseria meningitidis* conjugate vaccine comprising at least two capsular saccharides selected from the group consisting of *N. meningitidis* serogroup A capsular saccharide (MenA), *N. meningitidis* serogroup A capsular saccharide *N. meningitidis* serogroup C capsular saccharide (MenC), *N. meningitidis* serogroup W135 capsular saccharide (MenW135), and *N. meningitidis* serogroup Y capsular saccharide (MenY) conjugated separately to a second carrier protein, wherein the *Neisseria meningitidis* conjugate vaccine is co-administered with a vaccine comprising diphtheria toxoid and tetanus toxoid.

Step a) is an immunisation in the first year of life, typically taking place in human infants at an age of 0-8, 1-7 or 2-6 months. In an embodiment, the step a) immunisation comprises a *Haemophilus influenza* (Hib) saccharide conjugate and/or a *N. meningitidis* serogroup C (MenC) capsular saccharide conjugate and/or a *N. meningitidis* serogroup Y (MenY) capsular saccharide conjugate.

In an embodiment, the, or each of the conjugate(s) administered in step a) contains a carrier protein selected from tetanus toxoid, diphtheria toxoid or CRM197. In a preferred embodiment, where multiple conjugates are administered in step a), the same type of carrier protein is independently conjugated to each saccharide. In a preferred embodiment the first carrier protein is tetanus toxoid.

In an embodiment, the immunisation of step a) involves the administration of 2 or 3 doses of the bacterial saccharide conjugate(s), for example by immunising a human infant at 2, 4 and 6 months of age.

In an embodiment during step a) the bacterial capsular saccharide conjugate(s), for example Hib, MenC and/or MenY are administered at the same time as a vaccine comprising diphtheria, tetanus and pertussis antigens (DTP). The diphtheria antigen is typically diphtheria toxoid, the tetanus antigen is typically tetanus toxoid and the pertussis antigen may be wholecell pertussis or acellular pertussis, optionally comprising one or more of pertussis toxoid, FHA or pertactin. In an embodiment, the DTP vaccine further comprises a hepatitis B surface antigen and/or IPV. In an embodiment, the immunisation of step a) administers a HibMenCY-TT vaccine containing 2.5 µg of Hib PRP conjugated to tetanus toxoid and 5 µg of each of MenC and Y capsular saccharide conjugated to tetanus toxoid with a total TT content of 5-40, 10-30, 15-20 µg or about 18 µg.

Step b) involves immunising the same human patient in the second year of life, i.e. between 12 and 24, preferably 13 and 20, 12 and 18, 14 and 18 or 15-18 months of age. The step b) immunisation involves coadminstration of i) a multivalent *N. meningitidis* capsular saccharide conjugate vaccine with ii) a vaccine comprising diphtheria toxoid and tetanus toxoid. The multivalent *N. meningitidis* capsular saccharide conjugate vaccine comprises at least two of MenA, MenC, MenW135 and MenY; for example, conjugates of: serogroup C and Y capsular polysaccharides (MenCY), serogroup C and A capsular polysaccharides (MenAC), serogroup C and W135 capsular polysaccharides (MenCW), serogroup A and Y capsular polysaccharide (MenAY), serogroup A and W135 capsular polysaccharides (MenAW), serogroup W135 and Y capsular polysaccharides (Men WY), serogroup A, C and W135 capsular polysaccharide (MenACW), serogroup A, C and Y capsular polysaccharides (MenACY); serogroup A, W135 and Y capsular polysaccharides (MenAWY), serogroup C, W135 and Y capsular polysaccharides (MenCWY); or serogroup A, C, W135 and Y capsular polysaccharides (MenACWY).

In an embodiment, the multivalent *N. meningitidis* capsular saccharide conjugate vaccine uses a carrier protein (second carrier protein) that is selected from the group consisting of tetanus toxoid, diphtheria toxoid or CRM197. In an embodiment, the second carrier is tetanus toxoid. In a preferred embodiment, the first carrier protein and the second carrier protein are the same, preferably tetanus toxoid.

In an embodiment, the coadministered vaccine containing diphtheria toxoid and tetanus toxoid is a DTP vaccine additionally containing pertussis components which are whole cell pertussis or acellular pertussus, for example containing pertussis toxoid, FHA and pertactin. In an embodiment, the vaccine containing diphtheria toxoid and tetanus toxoid comprises further antigens, for example HBV and/or IPV.

In an embodiment, coadminstration of the multivalent *N. meningitidis* conjugate vaccine with a vaccine containing diphtheria toxoid and tetanus toxoid results in increased immunogenicity of at least one meningococcal components; for example, MenC, MenY, MenW135, MenC and MenY, MenC and MenW135 or MenC, MenW135 and MenY. In an embodiment, the increased immunogenicity is measured by SBA assay (optionally using a human complement source), optionally carried out on serum taken one month after vaccination with the multivalent *N. meningitidis* conjugate vaccine in the second year of life. In an embodiment, the GMT is increased following co-administration with a vaccine comprising diphtheria toxoid and tetanus toxoid by at least 10%, 20%, 30%, 40%, 50%, 60%, 70%, 80%, 90% or 100% compared to the GMT following administration for the multivalent *N. meningitidis* conjugate vaccine alone.

In an embodiment the carrier protein of step b) is present in the *Neisseria meningitidis* conjugate dose at a total dose of 10-100, 20-90, 20-80, 30-70, 35-60 or 40-50 μg. For example for a tetravalent *N. meningitidis* conjugate vaccine with TT, DT or CRM197 as carrier protein a total carrier protein dose of 20-80 μg is contemplated. For a bivalent *N. meningitis* conjugate vaccine a total carrier protein dose for TT, DT or CRM197 of 20-40 μg is contemplated.

The details set out above in relation to a method of immunisation are equally application to uses of a multivalent *N. meningitidis* conjugate vaccine in the prevention or treatment of *N. meningitidis* disease.

In an embodiment, the average size (or molecular weight) of at least one, two, three, four or each *N. meningitidis* polysaccharide is 50 KDa-1500 kDa, 50 kDa-500 kDa, 50 kDa-300 KDa, 101 kDa-1500 kDa, 101 kDa-500 kDa, or 101 kDa-300 kDa as determined by MALLS.

In an embodiment, the MenA polysaccharide, where present, has a molecular weight of 50-500 kDa, 50-100 kDa, 100-500 kDa, 55-90 KDa, 60-70 kDa or 70-80 kDa or 60-80 kDa as determined by MALLS.

In an embodiment, the MenC polysaccharide, where present, has a molecular weight of 100-200 kDa, 50-100 kDa, 100-150 kDa, 101-130 kDa, 150-210 kDa or 180-210 kDa as determined by MALLS.

In an embodiment the MenY polysaccharide, where present, has a molecular weight of 60-190 kDa, 70-180 kDa, 80-170 kDa, 90-160 kDa, 100-150 kDa or 110-140 kDa, 50-100 kDa, 100-140 kDa, 140-170 kDa or 150-160 kDa as determined by MALLS.

In an embodiment the MenW polysaccharide, where present, has a molecular weight of 60-190 kDa, 70-180 kDa, 80-170 kDa, 90-160 kDa, 100-150 kDa, 110-140 kDa, 50-100 kDa or 120-140 kDa as determined by MALLS.

The molecular weight or average molecular weight of a polysaccharide herein refers to the weight-average molecular weight (Mw) of the polysaccharide measured prior to conjugation and is measured by MALLS.

The MALLS technique is well known in the art and is typically carried out as described in example 2. For MALLS analysis of meningococcal saccharides, two columns (TSKG6000 and 5000PWxI TOSOH Bioscience) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm).

In an embodiment the *N. meningitidis* polysaccharides are native polysaccharides or native polysaccharides which have reduced in size during a normal extraction process.

In an embodiment, the *N. meningitidis* polysaccharides are sized by mechanical cleavage, for instance by microfluidisation or sonication. Microfluidisation and sonication have the advantage of decreasing the size of the larger native polysaccharides sufficiently to provide a filterable conjugate. Sizing is by a factor of no more than ×20, ×10, ×8, ×6, ×5, ×4, ×3, ×2 or ×1.5.

In an embodiment, the immunogenic composition comprises *N. meningitidis* conjugates that are made from a mixture of native polysaccharides and polysaccharides that are sized by a factor of no more than ×20. For example, polysaccharides from MenC and/or MenA are native. For example, polysaccharides from MenY and/or MenW are sized by a factor of no more than ×20, ×10, ×8, ×6, ×5, ×4, ×3, ×2 or ×1.5. For example, an immunogenic composition contains a conjugate made from MenY and/or MenW and/or MenC and/or MenA which is sized by a factor of no more then ×20, ×10, ×8, ×6, ×5, ×4, ×3, ×2 or ×1.5 and/or is microfluidised. For example, an immunogenic composition contains a conjugate made from native MenA and/or MenC and/or MenW and/or MenY. For example, an immunogenic composition comprises a conjugate made from native MenC. For example, an immunogenic composition comprises a conjugate made from native MenC and MenA which is sized by a factor of no more than ×20, ×10, ×8, ×6, ×5, ×4, ×3, ×2 or ×1.5 and/or is microfluidised. For example, an immunogenic composition comprises a conjugate made from native MenC and MenY which is sized by a factor of no more than ×20, ×10, ×8, ×6, ×5, ×4, ×3, ×2 or ×1.5 and/or is microfluidised.

In an embodiment, the polydispersity of the polysaccharide is 1-1.5, 1-1.3, 1-1.2, 1-1.1 or 1-1.05 and after conjugation to a carrier protein, the polydispersity of the conjugate is 1.0-2.5, 1.0-2.0. 1.0-1.5, 1.0-1.2, 1.5-2.5, 1.7-2.2 or 1.5-2.0. All polydispersity measurements are by MALLS.

Polysaccharides are optionally sized up to 1.5, 2, 4, 6, 8, 10, 12, 14, 16, 18 or 20 times from the size of the polysaccharide isolated from bacteria.

In an embodiment, the multivalent *N. meningitidis* conjugate vaccine further comprises an antigen from *N. meningitidis* serogroup B. The antigen is optionally a capsular polysaccharide from *N. meningitidis* serogroup B (MenB) or a sized polysaccharide or oligosaccharide derived therefrom. The antigen is optionally an outer membrane vesicle preparation from *N. meningitidis* serogroup B as described in EP301992, WO 01/09350, WO 04/14417, WO 04/14418 and WO 04/14419.

In an embodiment, the multivalent *N. meningitidis* conjugate vaccine further comprises a *H. influenzae* b (Hib) capsular saccharide conjugated to a carrier protein.

The *N. meningitidis* polysaccharide(s) (and optionally Hib capsular saccharide) included in pharmaceutical compositions of the invention are conjugated to a carrier protein such as tetanus toxoid, tetanus toxoid fragment C, non-toxic mutants of tetanus toxin, diphtheria toxoid, CRM197, other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843, 711].

In an embodiment, the multivalent *N. meningitidis* conjugate vaccine of the invention uses the same carrier protein (independently) in at least two, three, four or each of the *N. meningitidis* polysaccharides. In an embodiment where Hib is present, Hib may be conjugated to the same carrier protein as the at least one, two, three, four or each of the *N. meningitidis* polysaccharides. For example, 1, 2, 3 or 4 of the *N. meningitidis* polysaccharides are independently conjugated to tetanus toxoid to make 1, 2, 3 or 4 conjugates.

In an embodiment, a single carrier protein may carry more than one saccharide antigen (WO 04/083251). For example, a single carrier protein might be conjugated to MenA and MenC; MenA and MenW; MenA and MenY; MenC and MenW; MenC and MenY; Men W and MenY; MenA, MenC and MenW; MenA, MenC and MenY; MenA, MenW and MenY; MenC, MenW and MenY; MenA, MenC, MenW and MenY; Hib and MenA; Hib and MenC; Hib and MenW; or Hib and MenY.

The multivalent N. meningitidis conjugate vaccine optionally comprises at least one meningococcal saccharide (for example MenA; MenC; MenW; MenY; MenA and MenC; MenA and MenW; MenA and MenY; MenC and Men W; Men C and MenY; Men W and MenY; MenA, MenC and MenW; MenA, MenC and MenY; MenA, MenW and MwnY; MenC, MenW and MenY or MenA, MenC, MenW and MenY) conjugate having a ratio of Men saccharide to carrier protein (particularly tetanus toxoid) of between 1:5 and 5:1, between 1:2 and 5:1, between 1:0.5 and 1:2.5 or between 1:1.25 and 1:2.5 (w/w).

The ratio of saccharide to carrier protein (w/w) in a conjugate may be determined using the sterilized conjugate. The amount of protein is determined using a Lowry assay (for example Lowry et al (1951) J. Biol. Chem. 193, 265-275 or Peterson et al Analytical Biochemistry 100, 201-220 (1979)) and the amount of saccharide is determined using ICP-OES (inductively coupled plasma-optical emission spectroscopy) for MenA, DMAP assay for MenC and Resorcinol assay for MenW and MenY (Monsigny et al (1988) Anal. Biochem. 175, 525-530).

In an embodiment, the N. meningitidis capsular saccharide(s) and/or the Hib saccharide is conjugated to the carrier protein via a linker, for instance a bifunctional linker. The linker is optionally heterobifunctional or homobifunctional, having for example a reactive amino group and a reactive carboxylic acid group, 2 reactive amino groups or two reactive carboxylic acid groups. The linker has for example between 4 and 20, 4 and 12, 5 and 10 carbon atoms. A possible linker is ADH. Other linkers include B-propionamido (WO 00/10599), nitrophenyl-ethylamine (Gever et al (1979) Med. Microbiol. Immunol. 165; 171-288), haloalkyl halides (U.S. Pat. No. 4,057,685), glycosidic linkages (U.S. Pat. Nos. 4,673,574, 4,808,700), hexane diamine and 6-aminocaproic acid (U.S. Pat. No. 4,459,286).

The polysaccharide conjugates used in the invention may be prepared by any known coupling technique. The conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a holoacetylated carrier protein (for example using iodoacetimide or N-succinimidyl bromoacetatebromoacetate). Optionally, the cyanate ester (optionally made by CDAP chemistry) is coupled with hexane diamine or ADH and the amino-derivatised saccharide is conjugated to the carrier protein using carbodiimide (e.g. EDAC or EDC) chemistry. Such conjugates are described in PCT published application WO 93/15760 Uniformed Services University and WO 95/08348 and WO 96/29094.

Other suitable techniques use carbiinides, hydrazides, active esters, norborane, p-nitrobenzoic acid, N-hydroxysuccinimide, S-NHS, EDC, TSTU. Many are described in WO 98/42721. Conjugation may involve a carbonyl linker which may be formed by reaction of a free hydroxyl group of the saccharide with CDI (Bethell et al J. Biol. Chem. 1979, 254; 2572-4, Hearn et al J. Chromatogr. 1981. 218; 509-18) followed by reaction of with a protein to form a carbamate linkage. This may involve reduction of the anomeric terminus to a primary hydroxyl group, optional protection/deprotection of the primary hydroxyl group' reaction of the primary hydroxyl group with CDI to form a CDI carbamate intermediate and coupling the CDI carbamate intermediate with an amino group on a protein.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide (or CDAP) activated saccharide derivatised with adipic acid hydrazide (ADH) to the protein carrier by Carbodiimide condensation (Chu C. et al Infect. Immunity, 1983 245 256), for example using EDAC.

In an embodiment, a hydroxyl group (optionally an activated hydroxyl group for example a hydroxyl group activated by a cyanate ester) on a saccharide is linked to an amino or carboxylic group on a protein either directly or indirectly (through a linker). Where a linker is present, a hydroxyl group on a saccharide is optionally linked to an amino group on a linker, for example by using CDAP conjugation. A further amino group in the linker for example ADH) may be conjugated to a carboxylic acid group on a protein, for example by using carbodiimide chemistry, for example by using EDAC. In an embodiment, the Hib or N. meningitidis capsular polysaccharide(s) is conjugated to the linker first before the linker is conjugated to the carrier protein.

In an embodiment, the Hib saccharide, where present, is conjugated to the carrier protein using CNBr, or CDAP, or a combination of CDAP and carbodiimide chemistry (such as EDAC), or a combination of CNBr and carbodiimide chemistry (such as EDAC). Optionally Hib is conjugated using CNBr and carbodiimide chemistry, optionally EDAC. For example, CNBr is used to join the saccharide and linker and then carbodiimide chemistry is used to join linker to the protein carrier.

In an embodiment, at least one of the N. meningitidis capsular polysaccharides is directly conjugated to a carrier protein; optionally Men W and/or MenY and/or MenC saccharide(s) is directly conjugated to a carrier protein. For example MenW; MenY; MenC; MenW and MenY; MenW and MenC; MenY and MenC; or MenW, MenY and MenC are directly linked to the carrier protein. Optionally the at least one of the N. meningitidis capsular polysaccharides is directly conjugated by CDAP. For example MenW; MenY; MenC; MenW and MenY; MenW and MenC; MenY and MenC; or MenW, MenY and MenC are directly linked to the carrier protein by CDAP (see WO 95/08348 and WO 96/29094). In an embodiment, all N. meningitidis capsular polysaccharides are conjugated to tetanus toxoid.

Optionally the ratio of Men W and/or Y saccharide to carrier protein is between 1:0.5 and 1:2 (w/w) and/or the ratio of MenC saccharide to carrier protein is between 1:0.5 and 1:4 or 1:1.25-1:1.5 or 1:0.5 and 1:1.5 (w/w), especially where these saccharides are directly linked to the protein, optionally using CDAP.

In an embodiment, at least one of the N. meningitidis capsular polysaccharide(s) is conjugated to the carrier protein via a linker, for instance a bifunctional linker. The linker is optionally heterobifunctional or homobifunctional, having for example a reactive amine group and a reactive carboxylic acid group, 2 reactive amine groups or 2 reactive carboxylic acid groups. The linker has for example between 4 and 20, 4 and 12, 5 and 10 carbon atoms. A possible linker is ADH.

In an embodiment, MenA; MenC; or MenA and MenC is conjugated to a carrier protein (for example tetanus toxoid) via a linker.

In an embodiment, at least one N. meningitidis polysaccharide is conjugated to a carrier protein via a linker using CDAP and EDAC. For example, MenA; MenC; or MenA and MenC are conjugated to a protein via a linker (for example those with two hydrazino groups at its ends such as ADH) using CDAP and EDAC as described above. For example, CDAP is used to conjugate the saccharide to a linker and EDAC is used to conjugate the linker to a protein. Optionally the conjugation via a linker results in a ratio of polysaccharide to carrier protein of between 1:0.5 and 1:6; 1:1 and 1:5 or 1:2 and 1:4, for MenA; MenC; or MenA and MenC.

In an embodiment, the MenA capsular polysaccharide, where present is at least partially O-acetylated such that at least 50%, 60%, 70%, 80%, 90%, 95% or 98% of the repeat units are O-acetylated at at least one position. O-acetylation is for example present at least at the O-3 position of at least 50%, 60%, 70%, 80%, 90%, 95% or 98% of the repeat units.

In an embodiment, the MenC capsular polysaccharide, where present is at least partially O-acetylated such that at least 30%, 40%, 50%, 60%, 70%, 80%, 90%, 95% or 98% of (α2→9)-linked NeuNAc repeat units are O-acetylated at at least one or two positions. O-acetylation is for example present at the O-7 and/or O-8 position of at least 30%. 40%, 50%, 60%, 70%, 80%, 90%, 95% or 98% of the repeat units.

In an embodiment, the MenW capsular polysaccharide, where present is at least partially O-acetylated such that at least 30%, 40%, 50%, 60%, 70%, 80%, 90%, 95% or 98% of the repeat units are O-acetylated at at least one or two positions. O-acetylation is for example present at the 0-7 and/or 0-9 position of at least 30%. 40%, 50%, 60%, 70%, 80%, 90%, 95% or 98% of the repeat units.

In an embodiment, the MenY capsular polysaccharide, where present is at least partially O-acetylated such that at least 20%, 30%, 40%, 50%, 60%, 70%, 80%, 90%, 95% or 98% of the repeat units are O-acetylated at at least one or two positions. O-acetylation is present at the 7 and/or 9 position of at least 20%, 30%, 40%, 50%, 60%, 70%, 80%, 90%, 95% or 98% of the repeat units.

The percentage of O-acetylation refers to the percentage of the repeat units containing 0-acetylation. This may be measured in the polysaccharide prior to conjugate and/or after conjugation.

The term "saccharide" includes polysaccharides or oligosaccharides. Polysaccharides are isolated from bacteria or isolated from bacteria and sized to some degree by known methods (see for example EP497524 and EP497525) and optionally by microfluidisation. Polysaccharides can be sized in order to reduce viscosity in polysaccharide samples and/or to improve filterability for conjugated products. Oligosaccharides are characterised by typically being hydrolysed polysaccharides with a low number of repeat units (typically 5-30 repeat units).

The mean dose is determined by adding the doses of all the further polysaccharides and dividing by the number of further polysaccharides. Further polysaccharides are all the polysaccharides within the immunogenic composition apart from Hib and can include N. meningitidis capsular polysaccharides. The "dose" is in the amount of immunogenic composition or vaccine that is administered to a human.

A Hib saccharide is the polyribosyl phosphate (PRP) capsular polysaccharide of Haemophilus influenzae type b or an oligosaccharide derived therefrom.

In an embodiment, the multivalent N. meningitidis conjugate vaccine contains each N. meningitidis capsular saccharide at a dose of between 0.1-20 µg; 1-10 µg; 2-10 µg, 2.5-5 µg, around or exactly 5 µg; or around or exactly 2.5 µg.

"Around" or "approximately" are defined as within 10% more or less of the given figure for the purposes of the invention.

In an embodiment of the invention, the saccharide dose of each of the at least two, three, four or each of the N. meningitidis saccharide conjugates is optionally the same, or approximately the same.

The multivalent N. meningitidis conjugate vaccine optionally contains MenA, MenC, MenW135 and MenY at saccharide dose ratios of 1:1:1:1 or 2:1:1:1 or 1:2:1:1 or 2:2:1:1 or 1:3:1:1 or 1:4:1:1 (w/w).

A vaccines used in the method or use of the invention optionally contain a pharmaceutically acceptable excipient.

In an embodiment the multivalent N. meningitidis conjugate vaccine is buffered at, or adjusted to, between pH 7.0 and 8.0, pH 7.2 and 7.6 or around or exactly pH 7.4.

The multivalent N. meningitidis conjugate vaccine is optionally lyophilised in the presence of a stabilising agent for example a polyol such as sucrose or trehalose.

Optionally, the multivalent N. meningitidis conjugate vaccine contains an amount of an adjuvant sufficient to enhance the immune response to the immunogen. Suitable adjuvants include, but are not limited to, aluminium salts (aluminium phosphate or aluminium hydroxide), squalene mixtures (SAF-1), muramyl peptide, saponin derivatives, mycobacterium cell wall preparations, monophosphoryl lipid A, mycolic acid derivatives, non-ionic block copolymer surfactants, Quil A, cholera toxin B subunit, polyphosphazene and derivatives, and immunostimulating complexes (ISCOMs) such as those described by Takahashi et al. (1990) Nature 344:873-875.

For the N. meningitidis or HibMen combinations discussed above, it may be advantageous not to use any aluminium salt adjuvant or any adjuvant at all.

As with all immunogenic compositions or vaccines, the immunologically effective amounts of the immunogens must be determined empirically. Factors to be considered include the immunogenicity, whether or not the immunogen will be complexed with or covalently attached to an adjuvant or carrier protein or other carrier, route of administrations and the number of immunising dosages to be administered. Such factors are known in the vaccine art and it is well within the skill of immunologists to make such determinations without undue experimentation.

The active agent can be present in varying concentrations in the pharmaceutical composition or vaccine of the invention. Typically, the minimum concentration of the substance is an amount necessary to achieve its intended use, while the maximum concentration is the maximum amount that will remain in solution or homogeneously suspended within the initial mixture. For instance, the minimum amount of a therapeutic agent is optionally one which will provide a single therapeutically effective dosage. For bioactive substances, the minimum concentration is an amount necessary for bioactivity upon reconstitution and the maximum concentration is at the point at which a homogeneous suspension cannot be maintained. In the case of single-dosed units, the amount is that of a single therapeutic application. Generally, it is expected that each dose will comprise 1-100 µg of protein antigen, optionally 5-50 µg or 5-25 µg. Examples of doses of bacterial saccharides are 10-20 μg, 5-10 μg, 2.5-5 μg or 1-2.5 μg. The preferred amount of the substance varies from substance to substance but is easily determinable by one of skill in the art.

The vaccine preparations of the present invention may be used to protect or treat a human patient susceptible to infection, by means of administering said vaccine via systemic or mucosal route. A human patient is optionally an infant (under 12 months), or a toddler (12-24, 12-16 or 12-14 months). These administrations may include injection via the intramuscular, intraperitoneal, intradermal or subcutaneous routes; or via mucosal administration to the oral/alimentary, respiratory, genitourinary tracts. In addition to a single route of administration, 2 different routes of administration may be used. For example, viral antigens may be administered ID (intradermal), whilst bacterial proteins may be administered IM (intramuscular) or IN (intranasal). If saccharides are present, they may be administered IM (or ID) and bacterial proteins may be administered IN (or ID). In addition, the vaccines of the invention may be administered IM for priming doses and IN for booster doses.

The inventors have further determined that a later booster dose of a Neisseria meningitidis conjugate vaccine comprising at least two capsular saccharides selected from the group consisting of N. meningitidis serogroup A capsular saccharide (MenA), N. meningitidis serogroup C capsular saccharide (MenC), N. meningitidis serogroup W135 capsular saccharide (MenW135) and N. meningitidis serogroup Y capsular saccharide (MenY) can produce an even stronger immune response against capsular saccharide antigens. The data provided in example 3 show that a booster immunisation given several years following an initial immunisation gives a much higher GMT as assessed by SBA assay. Additional booster doses of meningococcal conjugate vaccines could extend the duration of vaccine-induced protection. An additional booster doses can be considered to be both an independent aspect of the invention or a further step of the coadministration aspect of the invention.

Accordingly, there is provided a method of immunising against Neisseria meningitidis infection comprising the steps of immunising a human patient at an age of between 12 and 24 months with a multivalent N. meningitidis conjugate vaccine comprising at least two capsular saccharides selected from the group consisting of N. meningitidis serogroup A capsular saccharide (MenA), N. meningitidis serogroup C capsular saccharide (MenC), N. meningitidis serogroup W135 capsular saccharide (MenW135), and N. meningitidis serogroup Y capsular saccharide (MenY) conjugated separately to a carrier protein and re-immunising the human patient at an age of between 4 and 20, 5 and 15, 5 and 11, 5 and 9 or 5 and 6 years with a boosting N. meningitidis conjugate vaccine comprising at least two of MenA, MenC, MenW135 and MenY, each conjugated separately to a carrier protein.

In an embodiment, the multivalent N. meningitidis conjugate vaccine comprises MenC and MenY conjugates and/or the boosting N. meningitidis conjugate vaccines comprises MenC and MenY conjugates.

In an embodiment, the multivalent N. meningitidis conjugate vaccine comprises MenA, MenC, MenW135 and MenY conjugates and/or the boosting N. meningitidis conjugate vaccine comprises MenA, MenC, MenW135 and MenY conjugates.

In an embodiment, each capsular saccharide of the boosting N. meningitidis conjugate vaccine is conjugated to a carrier protein selected from the group consisting of tetanus toxoid, diphtheria toxoid or CRM197, preferably the carrier protein is tetanus toxoid or CRM197, more preferably the carrier protein is tetanus toxoid.

In an embodiment, each capsular saccharide of the multivalent N. meningitidis conjugate vaccine is conjugated to a carrier protein selected from the group consisting of tetanus toxoid, diphtheria toxoid or CRM197, preferably the carrier protein is tetanus toxoid or CRM197, more preferably the carrier protein is tetanus toxoid.

It will be understood that the attributes of the meningococcal saccharides and conjugates set out above for the initial aspects of the invention are also applicable to the second aspect of the invention. Accordingly, the descriptions of meningococcal saccharides and conjugates set out above are optionally present in the multivalent N. meningitidis conjugate vaccine and the boosting N. meningitidis conjugate vaccine.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The terms "comprising", "comprise" and "comprises" herein are intended by the inventors to be optionally substitutable with the terms "consisting of", "consist of" and "consists of", respectively, in every instance.

All references or patent applications cited within this patent specification are incorporated by reference herein.

In order that this invention may be better understood, the following examples are set forth. These examples are for purposes of illustration only, and are not to be construed as limiting the scope of the invention in any manner.

EXAMPLES

Example 1

Study Design

This Phase III, randomized, controlled study was conducted in 59 centers in the US in accordance with Good Clinical Practice and the Declaration of Helsinki (1996 Somerset West). Written informed consent was obtained from each subject's parent/guardian prior to enrollment.

Figure 1:
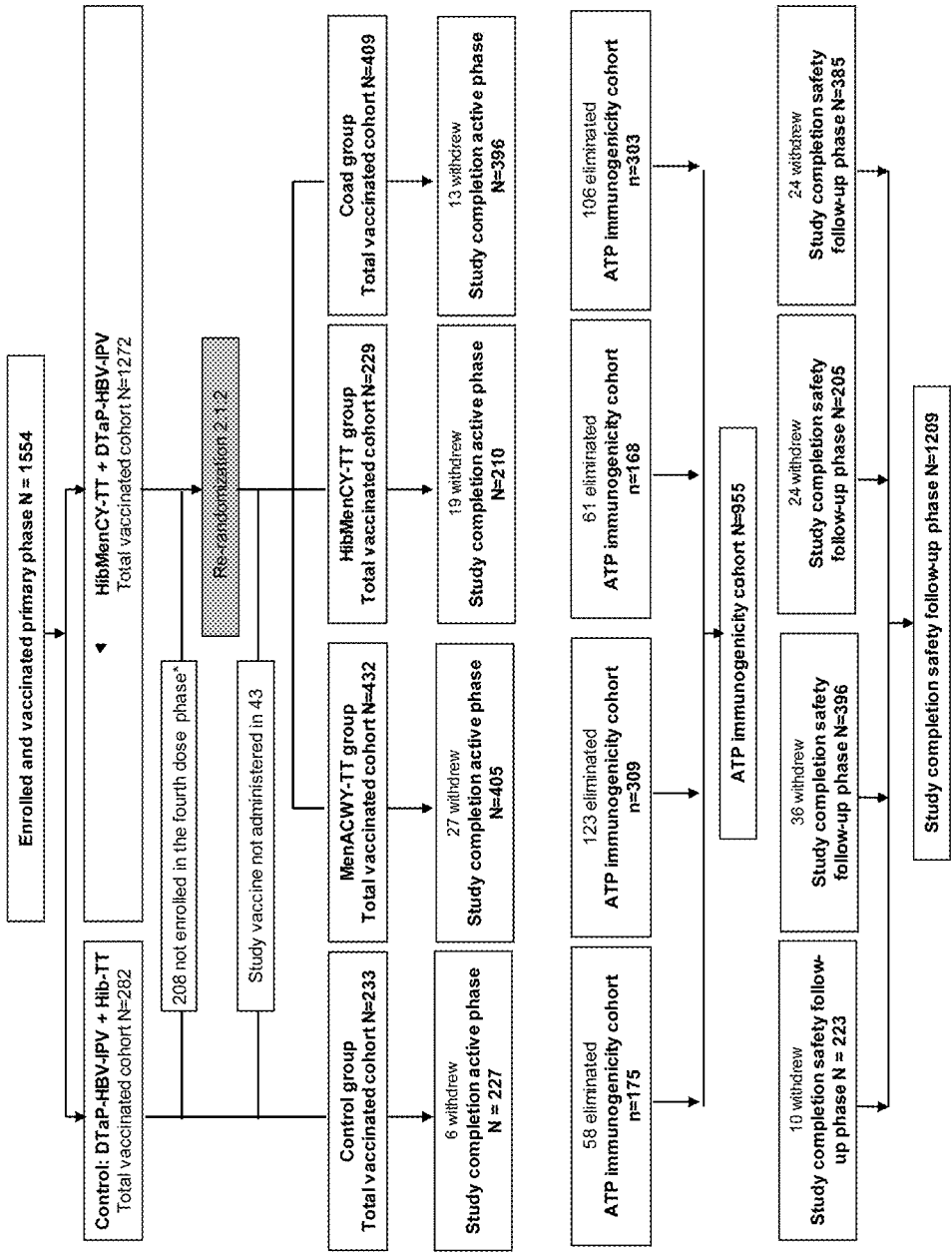
FIG. 1: Subject flow through the study

Healthy infants were enrolled and randomized 5:1 to vaccination at 2, 4 and 6 months of age with HibMenCY-TT and DTaP-HBV-IPV, or Hib-TT+DTaP-HBV-IPV (Table 1, FIG. 1). At 12-15 months of age (Fourth dose phase), children vaccinated with HibMenCY-TT+DTaP-HBV-IPV were re-randomized (2:2:1) to receive MenACWY-TT at 12-15 months of age followed by DTaP at 15-18 months (MenACWY-TT group); MenACWY-TT co-administered with DTaP at 15-18 months of age (Coad group); or HibMenCY-TT at 12-15 months of age followed by DTaP at 15-18 months (HibMenCY-TT group). Hib-TT+DTaP-HBV-IPV-primed children were not re-randomized and received DTaP at 15-18 months of age (Control group). Subjects in the Coad, MenACWT-TT and Control groups did not receive Hib booster vaccination because of an ongoing shortage of Hib conjugate vaccine in the US at the time of study conduct. Hib booster vaccinations were deferred until such time as Hib conjugate vaccine was once again available [25]. The study was conducted prior to the availability of a meningococcal conjugate vaccine licensed in the US for use in children<2 years of age; therefore the Control group did not receive meningococcal vaccination during the study. All subjects were permitted to receive routine vaccines recommended by ACIP.

The study was single-blind in the primary phase due to the different appearance of the vaccines. Prior to the fourth dose parents/guardians were informed which vaccines their child had received in the primary phase, and were aware of their treatment group in the fourth dose phase, due to the differing number of vaccines and serum sampling time points for the various treatment groups.

A randomization list was used to number the vaccines. Random assignment for each study phase was performed using a central, web-based system which included a minimization procedure to ensure balanced allocation between groups at individual centers.

Study Subjects and Vaccines

Participants were healthy infants between 6-12 weeks of age, born after at least 36 weeks of gestation. Exclusion criteria included prior receipt of any blood product since birth, or receipt of vaccines other than pneumococcal conjugate vaccine or human rotavirus vaccine within 30 days of the first dose. A birth dose of hepatitis B vaccine was allowed. A history of disease due to N. meningitidis, Hib, diphtheria, tetanus, pertussis, hepatitis B, or polio, or vaccination against any of these diseases performed outside of the study resulted in exclusion from the primary and fourth dose phases. For inclusion in the fourth dose phase, subjects had to have received all 3 primary vaccination doses.

One 0.5 ml dose of HibMenCY-TT contained 2.5 μg of Hib polyribosylribitol phosphate (PRP) conjugated to TT, and 5 μg each of MenC polysaccharide and MenY polysaccharide conjugated to TT (total TT content~18 μg). One 0.5 ml dose of MenACWY-TT contained 5 μg of each meningococcal serogroup A, C, W-135 and Y polysaccharide conjugated to TT (total TT content~44 μg). The lyophilised meningococcal vaccines were reconstituted with sterile saline for injection, and were administered intramuscularly into the left thigh or arm.

The composition of the licensed DTaP-HBV-IPV (Pediarix™, GlaxoSmithKline Vaccines) and Hib-TT (ActHIB™, Sanofi Pasteur) vaccines is described elsewhere [10]. The composition of DTaP (Infanrix™, GlaxoSmithKline Vaccines) is the same as the DTaP component of DTaP-HBV-IPV.

Study Objectives

The primary objectives were 1) To demonstrate the non-inferiority of MenACWY-TT with and without co-administration of DTaP to a fourth dose of HibMenCY-TT in terms of the percentage of subjects with serum bactericidal activity (using a human complement source: hSBA) titers≥1:8 and geometric mean titers (GMTs) for serogroups C and Y; 2) To demonstrate the immunogenicity of a single dose of MenACWY-TT with or without co-administration of DTaP in terms of the percentage of subjects with hSBA titers≥1:8 for serogroups A and W-135; and 3) To demonstrate the non-inferiority of DTaP co-administered with MenACWY-TT versus DTaP administration alone in terms of the percentage of subjects with anti-diphtheria and anti-tetanus antibody concentrations≥1.0 IU/ml and anti-pertussis geometric mean concentrations. This paper describes the meningococcal endpoints according to the pre-defined statistical criteria. Endpoints and immune responses are summarized in Table 2. The endpoints related to the DTaP booster vaccine are reported elsewhere [24].

Immunogenicity Assessment

Blood samples were collected from subjects one month after vaccination (Table 1) and prior to vaccination in the Coad group at 15-18 months of age (to assess hSBA persistence at 15-18 months of age after 3-dose infant vaccination with HibMenCY-TT).

Safety and Reactogenicity Assessment

Specific local and general symptoms were recorded by parents on diary cards for 8 days (Day 0-7) after the fourth dose vaccination. All other adverse events (AEs) were recorded for 31 days after vaccination. Serious adverse events (SAEs) and the occurrence of specific AEs indicating new onset of chronic illness, and conditions prompting visits to the Emergency Room (ER) were reported from dose 1 until 6 months after the last vaccination via standardized telephone script. The occurrence of rashes was recorded during the fourth dose phase. An SAE was defined as an event resulting in death or that was life-threatening; an event requiring hospitalization or prolongation of existing hospitalization; an event resulting in disability or incapacity of the subject; or any other event considered serious by the investigator.

Statistical Analyses

The analysis of immunogenicity was conducted on the According to Protocol (ATP) immunogenicity cohort that included all vaccinated subjects who complied with protocol-defined procedures. The primary objectives were assessed in a hierarchical manner; that is, an objective could only be considered formally met after all previous objectives were met.

Collection of a pre-vaccination blood sample in the Coad group (Table 1) allowed calculation of vaccine response rates and GMT ratios before and after vaccination in this group. A vaccine response was defined as an antibody titer 1:8 post-vaccination in initially seronegative subjects, and a ≥4 fold increase in the pre-vaccination antibody titer in initially seropositive subjects.

Potential differences between groups were highlighted in exploratory analyses if the asymptotic standardized 95% confidence interval (CI) for the difference between 2 groups in percentages of subjects reaching specified cutoffs did not include 0, or if the 95% CI for the GMT ratio between groups did not include 1. These exploratory analyses should be interpreted with caution considering that there was no adjustment for multiplicity.

The analysis of safety was performed on the total vaccinated cohort that included all vaccinated subjects. The incidence and intensity of symptoms were calculated with exact 95% CI for each group.

Analyses were performed using SAS® software version 9.1 (SAS Institute Inc., Cary, NC, United States) and Proc-StatXact 7.0.

Results

Study Subjects

A total of 1554 subjects were enrolled and vaccinated in the primary vaccination phase, of which 1447 completed this study phase. For the Fourth dose phase 1303 toddlers were enrolled and vaccinated (FIG. 1), of which 1238 subjects completed the Fourth dose vaccination phase of the study and 1209 completed the extended safety follow-up phase. A summary of the reasons subjects withdrew from the study or were eliminated from the ATP cohorts is given in Table 3 (supplementary). Two subjects, one from the MenACWY-TT group and one from the HibMenCY-TT group, withdrew during the Fourth dose vaccination phase due to an AE. Both subjects experienced a febrile convulsion prior to the scheduled fifth dose of DTaP: one with onset 38 days after the fourth dose and one with onset 43 days after the fourth dose. Neither event was considered to be related to vaccination by the investigator. There were 955 subjects in the ATP immunogenicity cohort. There were more males than females in the Co-ad group (165 versus 138, respectively) and more females than males in the Control group (97 versus 78, respectively). Study groups were otherwise comparable in terms of demographic characteristics (Table 4: supplementary).

Immunogenicity

After vaccination with HibMenCY-TT or MenACWY-TT at 12-15 months of age or with MenACWY-TT+DTaP at 15-18 months of age, 100% of subjects had hSBA titers≥1:8 for serogroups C and Y (FIG. 2), against which they had been previously primed. At least 96.1% of subjects vaccinated with MenACWY-TT also had hSBA titers≥1:8 for serogroups A and W-135 (FIG. 2). Very few subjects (≤7.8%) in the Control group had hSBA titers≥1:8 for any vaccine serogroup.

Exploratory analyses did not detect any differences between the MenACWY-TT and Coad groups compared to the HibMenCY-TT group for serogroups C and Y in terms of the percentage of subjects with hSBA titers≥1:8, one month after vaccination. However, the results suggested higher post-vaccination GMTs: 1) for serogroups C and Y in the MenACWY-TT and Coad groups compared to the HibMenCY-TT group and 2) for serogroups C, W-135 and Y in the Coad group compared to the MenACWY-TT group (FIG. 3).

The percentage of subjects in the Coad group with a vaccine response was 95.9% (95% CI 92.3%; 98.1%) for serogroup A, 99.2% (97.3%; 99.9%) for serogroup C, 97.7% (94.8%; 99.3%) for serogroup W-135 and 98.9% (96.8%; 99.8%) for serogroup Y. At least 96.1% of initially seronegative subjects had a vaccine response against one or more serogroups.

Prior to vaccination in the Coad group, 90.7% and 96.3% of subjects maintained seroprotective hSBA titers (1:4) against serogroups C and Y following 3-dose priming with HibMenCY-TT. In the Coad group, GMTs increased from pre to post vaccination by 107-fold for serogroup C and 53-fold for serogroup Y, indicative of a booster response following HibMenCY-TT priming; and by 44-fold for serogroup A and 244-fold for serogroup W-135, showing good immunogenicity to the first exposure to these vaccine antigens.

Post-dose 4 seroprotection rates and GMTs to serogroup W-135 were high in the MenACWY-TT and Coad groups, as well as in HibMenCY-TT recipients who did not receive the W-135 vaccine antigen at dose 4. No response to serogroup W-135 was observed in Controls.

Reactogenicity

The percentages of subjects reporting local and general symptoms were in the same range in the 3 investigational groups (FIG. 4). The percentages of subjects reporting SAEs, new onset of chronic disease and AEs results in an ER visit from the onset of primary vaccination until 6 months after the fourth dose were similar across the 3 groups (Table 5). Three SAEs reported in two subjects were considered to be vaccine related: There was one case of a floppy infant that occurred 47 days after dose 4 (Coad group), which resolved after 2 days. In addition, there was one reported case of convulsion occurred 65 days after the first primary vaccination dose (HibMenCY-TT group) that resolved in an infant who later died of a second SAE (sudden infant death syndrome) 89 days post-dose 1. There were three other deaths during the study (all in the primary phase), none of which were considered to be vaccine related: one subject died from sudden infant death syndrome 33 days post-dose 1; one subject from dehydration, hemolytic uremic syndrome and septic shock 43 days post-dose 1, and one subject from leukemia (onset 57 days post-dose 3) and eventual respiratory failure.

Example 2

Determination of Molecular Weight Using MALLS

Detectors were coupled to a HPLC size exclusion column from which the samples were eluted. On one hand, the laser light scattering detector measured the light intensities scattered at 16 angles by the macromolecular solution and on the other hand, an interferometric refractometer placed on-line allowed the determination of the quantity of sample eluted. From these intensities, the size and shape of the macromolecules in solution can be determined.

The mean molecular weight in weight ($M_w$) is defined as the sum of the weights of all the species multiplied by their respective molecular weight and divided by the sum of weights of all the species.

a) Weight-average molecular weight: -Mw- $$M_w = \frac{\sum W_i \cdot M_i}{\sum W_i} = \frac{m_2}{m_1}$$

b) Number-average molecular weight: —Mn—

$$M_n = \frac{\sum N_i \cdot M_i}{\sum N_i} = \frac{m_1}{m_0}$$

c) Root mean square radius: -Rw- and $R^2w$ is the square radius defined by:

$$R^2 w$$

or $$(r^2)w = \frac{\sum m_i \cdot r_i^2}{\sum m_i}$$

($-m_i$- is the mass of a scattering centre i and $-r_i$- is the distance between the scattering centre i and the center of gravity of the macromolecule).

d) The polydispersity is defined as the ratio -Mw/Mn—.

Meningococcal polysaccharides were analysed by MALLS by loading onto two HPLC columns (TSKG6000 and 5000PWxl) used in combination. 25 µl of the polysaccharide were loaded onto the column and was eluted with 0.75 ml of filtered water. The polysaccharides are detected using a light scattering detector (Wyatt Dawn DSP equipped with a 10 mW argon laser at 488 nm) and an inferometric refractometer (Wyatt Otilab DSP equipped with a P100 cell and a red filter at 498 nm).

The molecular weight polydispersities and recoveries of all samples were calculated by the Debye method using a polynomial fit order of 1 in the Astra 4.72 software.

Example 3

Effect of Booster Immunisation

A further study evaluated antibody persistence 12 months after booster vaccination with a meningococcal serogroups A, C, W-135, Y conjugate vaccine (MenACWY-TT, GlaxoSmithKline Vaccines) compared to a meningococcal serogroup C conjugate vaccine (MenC-CRM$_{197}$, Wyeth LLC), in healthy children.

Methods:

In this phase III, open-label, controlled, multi-centre study in Finland (NCT00955682), children previously randomized (3:1) and primed with a single dose of MenACWY-TT or MenC-CRM$_{197}$ at age 12-23 months (NCT00474266) received a booster dose of the same vaccines 48 months post-priming. Immunogenicity was evaluated at month (M) 60 (12 months post-booster) with serum bactericidal antibody assays using rabbit (rSBA; cut-off 1:8) and human (hSBA; cut-off 1:4) complement. Vaccine-related serious adverse events (SAEs) were recorded until M60.

Results:

Of 293 boosted children, 286 returned at M60, with 277 included in the according-to-protocol cohort for persistence at M60 (MenACWY-TT: N=231; MenC-CRM$_{197}$: N=46). At M60, all MenACWY-TT recipients retained rSBA titres≥1:8 (except for MenC, 97.4%) and hSBA titres≥1:4 (except for MenA, 95.5%) (Table). hSBA geometric mean antibody titres (GMTs) at M60 declined compared to M49 (1 month post-booster), but were higher than after primary vaccination. MenC seropositivity rates and GMTs (rSBA, hSBA) were comparable between groups. No vaccine-related SAEs were reported.

CONCLUSION

Antibodies evaluated by rSBA and hSBA assays persisted for each serogroup in >97% of children 12 months after MenACWY-TT booster vaccination. These data indicate that additional booster doses of MenACWY-TT could extend the duration of vaccine-induced protection.

TABLE 6

Percentage of children with rSBA titres ≥1:8 and hSBA titres ≥1:4 and corresponding GMTs (ATP cohort for persistence at M60)

| Antibody | Group | rSBA | | | hSBA | | |
|---|---|---|---|---|---|---|---|
| | | N | % ≥1:8 (95% CI) | GMT (95% CI) | N | % ≥1:4 (95% CI) | GMT (95% CI) |
| MenA | MenACWY-TT | 231 | 100 (98.4-100) | 978.9 (860.2-1114.0) | 221 | 95.5 (91.8-97.8) | 88.0 (73.6-105.1) |
| MenC | MenACWY-TT | 231 | 97.4 (94.4-99.0) | 226.4 (183.7-279.0) | 228 | 100 (98.4-100) | 1342.3 (1134.6-1588.1) |
| | MenC-CRM$_{197}$ | 46 | 97.8 (88.5-99.9) | 320.9 (201.1-512.2) | 33 | 100 (89.4-100) | 931.1 (572.8-1513.4) |
| MenW-135 | MenACWY-TT | 231 | 100 (98.4-100) | 1390.7 (1203.2-1607.3) | 218 | 100 (98.3-100) | 2196.6 (1955.7-2467.2) |
| MenY | MenACWY-TT | 231 | 100 (98.4-100) | 1071.1 (924.9-1240.5) | 206 | 100 (98.2-100) | 1110.8 (987.5-1249.6) |

GMT = geometric mean antibody titre;
ATP = according-to-protocol;
M60 = Month 60, 12 months post-booster;
N = number of subjects with available results;
95% CI = 95% confidence interval rSBA assay performed at Public Health England; hSBA assay at GlaxoSmithKline Vaccines

TABLE 7

Percentage of subjects with hSBA titres equal to or above the cut-off values of 1:4 and 1:8 and GMTs (ATP cohort for persistence at Month 60)

| Antibody | Group | Timing | N | ≥1:4 | | 95% CI | | ≥1:8 | | 95% CI | | GMT | 95% CI | |
|---|---|---|---|---|---|---|---|---|---|---|---|---|---|---|
| | | | | n | % | LL | UL | n | % | LL | UL | value | LL | UL |
| hSBA-MenA | MenACWY-TT | PRE | 226 | 4 | 1.8 | 0.5 | 4.5 | 1 | 0.4 | 0.0 | 2.4 | 2.0 | 2.0 | 2.1 |
| | | POST | 220 | 185 | 84.1 | 78.6 | 88.7 | 178 | 80.9 | 75.1 | 85.9 | 23.7 | 19.5 | 28.7 |
| | | M24 | 191 | 52 | 27.2 | 21.0 | 34.1 | 47 | 24.6 | 18.7 | 31.3 | 4.1 | 3.4 | 4.9 |
| | | M36 | 210 | 77 | 36.7 | 30.1 | 43.6 | 72 | 34.3 | 27.9 | 41.1 | 5.6 | 4.5 | 6.8 |
| | | M48 | 203 | 56 | 27.6 | 21.6 | 34.3 | 55 | 27.1 | 21.1 | 33.8 | 4.6 | 3.7 | 5.5 |
| | | M49 | 214 | 213 | 99.5 | 97.4 | 100 | 213 | 99.5 | 97.4 | 100 | 1371.2 | 1149.7 | 1635.4 |
| | | M60 | 221 | 211 | 95.5 | 91.8 | 97.8 | 211 | 95.5 | 91.8 | 97.8 | 88.0 | 73.6 | 105.1 |
| | MenCCRM | PRE | 35 | 0 | 0.0 | 0.0 | 10.0 | 0 | 0.0 | 0.0 | 10.0 | 2.0 | 2.0 | 2.0 |
| | | POST | 34 | 0 | 0.0 | 0.0 | 10.3 | 0 | 0.0 | 0.0 | 10.3 | 2.0 | 2.0 | 2.0 |
| | | M24 | 30 | 2 | 6.7 | 0.8 | 22.1 | 0 | 0.0 | 0.0 | 11.6 | 2.1 | 1.9 | 2.3 |
| | | M36 | 29 | 5 | 17.2 | 5.8 | 35.8 | 4 | 13.8 | 3.9 | 31.7 | 2.7 | 2.1 | 3.4 |
| | | M48 | 29 | 4 | 13.8 | 3.9 | 31.7 | 4 | 13.8 | 3.9 | 31.7 | 2.8 | 2.0 | 3.9 |
| | | M49 | 30 | 4 | 13.3 | 3.8 | 30.7 | 4 | 13.3 | 3.8 | 30.7 | 2.7 | 2.0 | 3.6 |
| | | M60 | 28 | 3 | 10.7 | 2.3 | 28.2 | 3 | 10.7 | 2.3 | 28.2 | 2.5 | 1.9 | 3.2 |

TABLE 7-continued

Percentage of subjects with hSBA titres equal to or above the cut-off values of 1:4 and 1:8 and GMTs (ATP cohort for persistence at Month 60)

| | | | | | | ≥1:4 | | | | | ≥1:8 | | GMT | | |
|---|---|---|---|---|---|---|---|---|---|---|---|---|---|---|---|
| | | | | | | | 95% CI | | | | | 95% CI | | | 95% CI |
| Antibody | Group | Timing | N | n | % | LL | UL | n | % | LL | UL | value | LL | UL |
| hSBA-MenC | MenACWY-TT | PRE | 230 | 2 | 0.9 | 0.1 | 3.1 | 2 | 0.9 | 0.1 | 3.1 | 2.0 | 2.0 | 2.1 |
| | | POST | 219 | 215 | 98.2 | 95.4 | 99.5 | 214 | 97.7 | 94.8 | 99.3 | 181.5 | 154.5 | 213.2 |
| | | M24 | 181 | 157 | 86.7 | 80.9 | 91.3 | 155 | 85.6 | 79.7 | 90.4 | 48.7 | 37.5 | 63.1 |
| | | M36 | 211 | 168 | 79.6 | 73.5 | 84.8 | 162 | 76.8 | 70.5 | 82.3 | 33.3 | 25.5 | 43.5 |
| | | M48 | 211 | 153 | 72.5 | 66.0 | 78.4 | 152 | 72.0 | 65.5 | 78.0 | 30.1 | 22.4 | 40.5 |
| | | M49 | 221 | 221 | 100 | 98.3 | 100 | 221 | 100 | 98.3 | 100 | 15490.7 | 13389.3 | 17921.9 |
| | | M60 | 228 | 228 | 100 | 98.4 | 100 | 228 | 100 | 98.4 | 100 | 1342.3 | 1134.6 | 1588.1 |
| | MenC-CRM | PRE | 35 | 1 | 2.9 | 0.1 | 14.9 | 1 | 2.9 | 0.1 | 14.9 | 2.1 | 1.9 | 2.3 |
| | | POST | 34 | 28 | 82.4 | 65.5 | 93.2 | 28 | 82.4 | 65.5 | 93.2 | 43.5 | 23.6 | 80.2 |
| | | M24 | 26 | 13 | 50.0 | 29.9 | 70.1 | 11 | 42.3 | 23.4 | 63.1 | 8.1 | 4.1 | 15.7 |
| | | M36 | 29 | 11 | 37.9 | 20.7 | 57.7 | 11 | 37.9 | 20.7 | 57.7 | 5.6 | 3.3 | 9.6 |
| | | M48 | 33 | 15 | 45.5 | 28.1 | 63.6 | 15 | 45.5 | 28.1 | 63.6 | 10.7 | 4.8 | 23.8 |
| | | M49 | 35 | 35 | 100 | 90.0 | 100 | 35 | 100 | 90.0 | 100 | 8474.8 | 5787.3 | 12410.2 |
| | | M60 | 33 | 33 | 100 | 89.4 | 100 | 33 | 100 | 89.4 | 100 | 931.1 | 572.8 | 1513.4 |
| hSBA-MenW-135 | MenACWY-TT | PRE | 227 | 1 | 0.4 | 0.0 | 2.4 | 1 | 0.4 | 0.0 | 2.4 | 2.0 | 2.0 | 2.1 |
| | | POST | 212 | 177 | 83.5 | 77.8 | 88.2 | 176 | 83.0 | 77.3 | 87.8 | 47.7 | 37.4 | 60.9 |
| | | M24 | 190 | 176 | 92.6 | 87.9 | 95.9 | 173 | 91.1 | 86.1 | 94.7 | 81.5 | 64.9 | 102.5 |
| | | M36 | 212 | 173 | 81.6 | 75.7 | 86.6 | 173 | 81.6 | 75.7 | 86.6 | 53.6 | 41.7 | 69.0 |
| | | M48 | 171 | 139 | 81.3 | 74.6 | 86.8 | 138 | 80.7 | 74.0 | 86.3 | 48.3 | 36.9 | 63.4 |
| | | M49 | 203 | 203 | 100 | 98.2 | 100 | 203 | 100 | 98.2 | 100 | 13996.6 | 12637.4 | 15501.3 |
| | | M60 | 218 | 218 | 100 | 98.3 | 100 | 218 | 100 | 98.3 | 100 | 2196.6 | 1955.7 | 2467.2 |
| | MenCCRM | PRE | 35 | 0 | 0.0 | 0.0 | 10.0 | 0 | 0.0 | 0.0 | 10.0 | 2.0 | 2.0 | 2.0 |
| | | POST | 34 | 1 | 2.9 | 0.1 | 15.3 | 1 | 2.9 | 0.1 | 15.3 | 2.2 | 1.8 | 2.6 |
| | | M24 | 30 | 0 | 0.0 | 0.0 | 11.6 | 0 | 0.0 | 0.0 | 11.6 | 2.0 | 2.0 | 2.0 |
| | | M36 | 31 | 2 | 6.5 | 0.8 | 21.4 | 2 | 6.5 | 0.8 | 21.4 | 2.4 | 1.8 | 3.2 |
| | | M48 | 28 | 2 | 7.1 | 0.9 | 23.5 | 2 | 7.1 | 0.9 | 23.5 | 2.6 | 1.8 | 3.6 |
| | | M49 | 27 | 2 | 7.4 | 0.9 | 24.3 | 2 | 7.4 | 0.9 | 24.3 | 2.7 | 1.8 | 4.2 |
| | | M60 | 31 | 5 | 16.1 | 5.5 | 33.7 | 5 | 16.1 | 5.5 | 33.7 | 3.4 | 2.2 | 5.4 |
| hSBA-MenY | MenACWY-TT | PRE | 221 | 1 | 0.5 | 0.0 | 2.5 | 1 | 0.5 | 0.0 | 2.5 | 2.0 | 2.0 | 2.1 |
| | | POST | 212 | 168 | 79.2 | 73.2 | 84.5 | 168 | 79.2 | 73.2 | 84.5 | 30.8 | 24.4 | 38.8 |
| | | M24 | 167 | 141 | 84.4 | 78.0 | 89.6 | 141 | 84.4 | 78.0 | 89.6 | 55.4 | 42.1 | 72.9 |
| | | M36 | 209 | 151 | 72.2 | 65.7 | 78.2 | 148 | 70.8 | 64.1 | 76.9 | 32.5 | 24.7 | 42.8 |
| | | M48 | 131 | 85 | 64.9 | 56.1 | 73.0 | 85 | 64.9 | 56.1 | 73.0 | 29.9 | 20.3 | 44.1 |
| | | M49 | 184 | 184 | 100 | 98.0 | 100 | 184 | 100 | 98.0 | 100 | 6698.9 | 5934.8 | 7561.3 |
| | | M60 | 206 | 206 | 100 | 98.2 | 100 | 206 | 100 | 98.2 | 100 | 1110.8 | 987.5 | 1249.6 |
| | MenC-CRM | PRE | 35 | 1 | 2.9 | 0.1 | 14.9 | 1 | 2.9 | 0.1 | 14.9 | 2.3 | 1.7 | 3.0 |
| | | POST | 34 | 1 | 2.9 | 0.1 | 15.3 | 1 | 2.9 | 0.1 | 15.3 | 2.3 | 1.7 | 3.2 |
| | | M24 | 27 | 5 | 18.5 | 6.3 | 38.1 | 5 | 18.5 | 6.3 | 38.1 | 4.2 | 2.2 | 8.1 |
| | | M36 | 31 | 6 | 19.4 | 7.5 | 37.5 | 6 | 19.4 | 7.5 | 37.5 | 4.3 | 2.4 | 7.7 |
| | | M48 | 28 | 6 | 21.4 | 8.3 | 41.0 | 6 | 21.4 | 8.3 | 41.0 | 4.3 | 2.4 | 7.8 |
| | | M49 | 27 | 7 | 25.9 | 11.1 | 46.3 | 7 | 25.9 | 11.1 | 46.3 | 5.4 | 2.7 | 11.0 |
| | | M60 | 31 | 10 | 32.3 | 16.7 | 51.4 | 10 | 32.3 | 16.7 | 51.4 | 7.5 | 3.6 | 15.7 |

GMT = geometric mean antibody titre calculated on all subjects
N = number of subjects with available results
n/% = number/percentage of subjects with titre within the specified range
95% CI = 95% confidence interval;
LL = Lower Limit,
UL = Upper Limit
PRE = Day 0, pre-primary vaccination
POST = 42 days post-primary vaccination with meningococcal vaccine
M24 = 24 months post-primary vaccination
M36 = 36 months post-primary vaccination
M48 = 48 months post-primary vaccination and pre-booster vaccination
M49 = one month post-booster vaccination (Month 49)
M60 = 12 months post-booster vaccination (Month 60)
Note:
At the 'POST' time point subjects from the MMRV Group in the primary study who were enrolled in the MenC-CRM Group in this persistence study had not yet received a meningococcal vaccine.

REFERENCES

[1] Rosenstein N E, Perkins B A, Stephens D S, Popovic T, Hughes J M. Meningococcal disease. N Engl J Med 2001; 344: 1378-1388.

[2] Cohn A C, MacNeil J R, Harrison L H, et al. Changes in *Neisseria meningitidis* disease epidemiology in the United States, 1998-2007: implications for prevention of meningococcal disease. Clin Infect Dis 2010; 50: 184-191.

[3] Harrison L H, Trotter C L, Ramsay M E. Global epidemiology of meningococcal disease. Vaccine 2009; 27: B51-63.

[4] Pollard A J. Global epidemiology of meningococcal disease and vaccine efficacy. Pediatr Infect Dis J 2004; 23: S274-279.

[5] Lingappa J R, Rosenstein N, Zell E R, Shutt K A, Schuchat A, Perkins B A. Surveillance for meningococcal disease and strategies for use of conjugate meningococcal vaccines in the United States. Vaccine 2001; 19: 4566-4575.

[6] Press Announcements—FDA approves new combination vaccine that protects children against two bacterial diseases. Available at: http://www.fda.gov/NewsEvents/Newsroom/PressAnnouncements/ucm308350.htm. Accessed 30 Jul. 2012.

[7] Bryant K A, Marshall G S, Marchant C D, et al. Immunogenicity and safety of *H influenzae* type b-*N meningitidis* C/Y conjugate vaccine in infants. Pediatrics 2011; 127: e1375-1385.

[8] Nolan T, Lambert S, Roberton D, et al. A novel combined *Haemophilus influenzae* type b-*Neisseria meningitidis* serogroups C and Y-tetanus-toxoid conjugate vaccine is immunogenic and induces immune memory when co-administered with DTPa-HBV-IPV and conjugate pneumococcal vaccines in infants. Vaccine 2007; 25: 8487-8499.

[9] Habermehl P, Leroux-Roels G, Sanger R, Machler G, Boutriau D. Combined *Haemophilus influenzae* type b and *Neisseria meningitidis* serogroup C (HibMenC) or serogroup C and Y-tetanus toxoid conjugate (and HibMenCY) vaccines are well-tolerated and immunogenic when administered according to the 2, 3, 4 months schedule with a fourth dose at 12-18 months of age. Hum Vaccin 2010; 6: 640-651.

[10] Marshall G S, Marchant C D, Blatter M, Friedland L R, Aris E, Miller J M. Co-administration of a novel *Haemophilus influenzae* type b and *Neisseria meningitidis* serogroups C and Y-tetanus toxoid conjugate vaccine does not interfere with the immune response to antigens contained in infant vaccines routinely used in the United States. Hum Vaccin 2011; 7: 258-264.

[11] Marchant C D, Miller J M, Marshall G S, et al. Randomized trial to assess immunogenicity and safety of *Haemophilus influenzae* type b and *Neisseria meningitidis* serogroups C and Y-tetanus toxoid conjugate vaccine in infants. Pediatr Infect Dis J 2010; 29: 48-52.

[12] Rinderknecht S, Bryant K, Nolan T, et al. The safety profile of *Hemophilus influenzae* type b-*Neisseria meningitidis* serogroups C and Y tetanus toxoid conjugate vaccine (HibMenCY). Hum Vaccin Immunother 2012; 8(3). Available at: http://www.ncbi.nlm.nih.gov/pubmed/22327493. Accessed 29 Feb. 2012.

[13] Marshall G S, Marchant C D, Blatter M, et al. Immune response and one-year antibody persistence after a fourth dose of a novel *Haemophilus influenzae* type b and *Neisseria meningitidis* serogroups C and Y-tetanus toxoid conjugate vaccine (HibMenCY) at 12 to 15 months of age. Pediatr Infect Dis J 2010; 29: 469-471.

[14] Nolan T, Richmond P, Marshall H, et al. Immunogenicity and safety of an investigational combined *Haemophilus influenzae* type B-*Neisseria meningitidis* serogroups C and Y-tetanus toxoid conjugate vaccine. Pediatr Infect Dis J 2011; 30: 190-196.

[15] Recommendation of the Advisory Committee on Immunization Practices (ACIP) for use of quadrivalent meningococcal conjugate vaccine (MenACWY-D) among children aged 9 through 23 months at increased risk for invasive meningococcal disease. Available at: http://www.cdc.gov/mmwr/preview/mmwrhtml/mm6040a4.htm?s_cid=mm6040a4_e%0d%0a. Accessed 13 Jan. 2012.

[16] Ostergaard L, Lebacq E, Poolman J, Maechler G, Boutriau D. Immunogenicity, reactogenicity and persistence of meningococcal A, C, W-135 and Y-tetanus toxoid candidate conjugate (MenACWY-TT) vaccine formulations in adolescents aged 15-25 years. Vaccine 2009; 27: 161-168.

[17] Knuf M, Kieninger-Baum D, Habermehl P, et al. A dose-range study assessing immunogenicity and safety of one dose of a new candidate meningococcal serogroups A, C, W-135, Y tetanus toxoid conjugate (MenACWY-TT) vaccine administered in the second year of life and in young children. Vaccine 2010; 28: 744-753.

[18] Baxter R, Baine Y, Ensor K, Bianco V, Friedland L R, Miller J M. Immunogenicity and safety of an investigational quadrivalent meningococcal ACWY tetanus toxoid conjugate vaccine in healthy adolescents and young adults 10 to 25 years of age. Pediatr Infect Dis J 2011; 30: e41-48.

[19] Vesikari T, Karvonen A, Bianco V, Van der Wielen M, Miller J. Tetravalent meningococcal serogroups A, C, W-135 and Y conjugate vaccine is well tolerated and immunogenic when co-administered with measles-mumps-rubella-varicella vaccine during the second year of life: An open, randomized controlled trial. Vaccine 2011; 29: 4274-4284.

[20] Memish Z A, Dbaibo G, Montellano M, et al. Immunogenicity of a single dose of tetravalent meningococcal serogroups A, C, W-135, and Y conjugate vaccine administered to 2- to 10-year-olds is noninferior to a licensed-ACWY polysaccharide vaccine with an acceptable safety profile. Pediatr Infect Dis J 2011; 30: e56-62.

[21] Knuf M, Pantazi-Chatzikonstantinou A, Pfletschinger U, et al. An investigational tetravalent meningococcal serogroups A, C, W-135 and Y-tetanus toxoid conjugate vaccine co-administered with Infanrix™ hexa is immunogenic, with an acceptable safety profile in 12-23-month-old children. Vaccine 2011; 29: 4264-4273.

[22] Bermal N, Huang L-M, Dubey A, et al. Safety and immunogenicity of a tetravalent meningococcal serogroups A, C, W-135 and Y conjugate vaccine in adolescents and adults. Hum Vaccin 2011; 7: 239-247.

[23] Dbaibo G, Macalalad N, Reyes M R A-D L, et al. The immunogenicity and safety of an investigational meningococcal serogroups A, C, W-135, Y tetanus toxoid conjugate vaccine (ACWY-TT) compared with a licensed meningococcal tetravalent polysaccharide vaccine: A randomized, controlled non-inferiority study. Hum Vaccin Immunother 2012; 8. Available at: http://www.ncbi.nlm.nih.gov/pubmed/22485050. Accessed 22 Jun. 2012.

[24] Leonardi M, Latiolais T, Sarpong K, et al. Immunogenicity and reactogenicity of co-administration of Infanrix™ with meningococcal MenACWY-TT conjugate vaccine in toddlers primed with MenHibrix™ and Pediarix™'

[25] Interim recommendations for the use of *Haemophilus influenzae* type b (Hib) conjugate vaccines related to the recall of certain lots of Hib-containing vaccines (PedvaxHIB and Comvax). MMWR 2007; 56: 1318-1320.

[26] Schmitt H-J, Maechler G, Habermehl P, et al. Immunogenicity, reactogenicity, and immune memory after primary vaccination with a novel *Haemophilus influenzae*-*Neisseria meningitidis* serogroup C conjugate vaccine. Clin. Vaccine Immunol 2007; 14: 426-434.

[27] Kitchin N R E, Southern J, Morris R, et al. Evaluation of a diphtheria-tetanus-acellular pertussis-inactivated poliovirus-*Haemophilus influenzae* type b vaccine given concurrently with meningococcal group C conjugate vaccine at 2, 3 and 4 months of age. ArchDis Child 2007; 92: 11-16.

[28] Diez-Domingo J, Cantarino M V P, Torrentí J M B, et al. A randomized, multicenter, open-label clinical trial to assess the immunogenicity of a meningococcal C vaccine booster dose administered to children aged 14 to 18 months. Pediatr Infect Dis J 2010; 29: 148-152.

[29] Khatami A, Snape M D, John T, et al. Persistence of immunity following a booster dose of *Haemophilus influenzae* type B-Meningococcal serogroup C glycoconjugate vaccine: follow-up of a randomized controlled trial. Pediatr Infect Dis J 2011; 30: 197-202.

[30] Bhattacharjee A K, Jennings H J, Kenny C P, Martin A, Smith I C. Structural determination of the polysaccharide antigens of *Neisseria meningitidis* serogroups Y, W-135, and B01. Can J Biochem 1976; 54:1-8.

The invention claimed is:

1. A method of immunising against *Neisseria meningitidis* infection, comprising the steps of:
   (a) immunising a human patient at a first age of between 0 and 6 months with a bacterial saccharide conjugate vaccine comprising bacterial saccharides each separately conjugated to tetanus toxoid carrier proteins, wherein the bacterial saccharides consist essentially of (i) a *N. meningitidis* serogroup C (MenC) capsular saccharide and a *Haemophilus influenza* (Hib) saccharide or (ii) a *N. meningitidis* serogroup C (MenC) capsular saccharide, a *N. meningitidis* serogroup Y (MenY) capsular saccharide and a *Haemophilus influenza* (Hib) saccharide, and wherein the tetanus toxoid carrier protein is present at a total TT content of 5-40 idg per dose; and
   (b) immunising the human patient at a second age of between 13 and 20 months with a *Neisseria meningitidis* conjugate vaccine comprising *N. meningitidis* serogroup A capsular saccharide (MenA), *N. meningitidis* serogroup C capsular saccharide (MenC), *N. meningitidis* serogroup W135 capsular saccharide (MenW135), and *N. meningitidis* serogroup Y capsular saccharide (MenY) conjugated separately to a tetanus toxoid carrier protein which is present at a total dose of 30-80 μg, wherein the *Neisseria meningitidis* conjugate vaccine is co-administered with a vaccine comprising diphtheria, tetanus, and acellular pertussis antigens (DTPa),
   wherein co-administration of the *Neisseria meningitidis* conjugate vaccine with the vaccine comprising DTPa in step b) results in an at least 10% increase in immunogenicity against at least one of MenA, MenC, MenW135, and MenY compared to where the *Neisseria meningitidis* conjugate vaccine is administered alone, measured by Serum Bacteriocidal Assay (SBA).

2. The method of claim 1 wherein the immunisation of step a) involves the administration of 3 doses of the bacterial saccharide conjugate, optionally at 2, 4 and 6 months of age.

3. The method of claim 1 wherein the vaccine comprising DTPa contains a hepatitis B antigen.

4. The method of claim 1 wherein the vaccine comprising DTPa contains Inactivated Polio Virus (IPV).

5. The method of claim 1 wherein step b) immunises the human patient at between 13 and 18 months of age.

6. The method of claim 1 wherein step b) immunises the human patient at between 15-18 months of age.

7. The method according to claim 1 wherein the *Neisseria meningitidis* conjugate vaccine of step b) contains *N. meningitidis* capsular saccharides having an average size of above 50 kDa.

8. The method according to claim 1 wherein the *Neisseria meningitidis* conjugate vaccine of step b) contains *N. meningitidis* capsular saccharides each of which is either a native polysaccharide or is reduced in average size relative to a native polysaccharide by a factor of no more than 10 fold.

9. The method according to claim 1 wherein the *N. meningitidis* conjugate vaccine of step b) contains at least one *N. meningitidis* capsular saccharide which is a native polysaccharide.

10. The method according to claim 1 wherein the *N. meningitidis* conjugate vaccine of step b) contains at least one *N. meningitidis* capsular saccharide which is reduced in size by microfluidization.

11. The method according to claim 1 wherein the *N. meningitidis* conjugate vaccine of step b) contains at least one *N. meningitidis* capsular saccharide selected from the group consisting of MenY and MenW135 which are microfludized, optionally to reduce the average size no more than 10 fold relative to the native capsular polysaccharide.

12. The method according to claim 1 wherein the *N. meningitidis* conjugate vaccine of step b) contains at least one *N. meningitidis* capsular saccharide selected from the group consisting of MenA and MenC which is a native polysaccharide.

13. The method according to claim 1 wherein the *N. meningitidis* conjugate vaccine of step b) contains a MenA capsular saccharide having an average size of above 50 kDa.

14. The method according to claim 1 wherein the *N. meningitidis* conjugate vaccine of step b) contains a MenC capsular saccharide having an average size of above 50 kDa.

15. The method according to claim 1 wherein the *N. meningitidis* conjugate vaccine of step b) contains a MenY capsular saccharide, having an average size of above 50 kDa.

16. The method according to claim 1 wherein the *N. meningitidis* conjugate vaccine of step b) contains a MenW135 capsular saccharide having an average size of above 50 kDa.

17. The method according to claim 1 wherein the *N. meningitidis* conjugate vaccine of step b) contains *N. meningitidis* capsular saccharide conjugates, each having a polysaccharide:carrier ratio of 1:5-5:1 or 1:1-1:4(w/w).

18. The method according to claim 1 wherein at least one of the *N. meningitidis* capsular polysaccharides of the *N. meningitidis* conjugate vaccine of step (b) is directly conjugated to the tetanus toxoid carrier protein of the *N. meningitidis* conjugate vaccine of step (b).

19. The method according to claim 18 wherein the MenW135 and MenC and MenY capsular saccharides of the *N. meningitidis* conjugate vaccine of step (b) are directly conjugated to the tetanus toxoid carrier protein of the *N. meningitidis* conjugate vaccine of step (b).

20. The method according to claim 18 wherein the *N. meningitidis* conjugate vaccine of step b) contains at least one *N. meningitidis* capsular saccharide conjugate directly conjugated by 1-cyano-4-dimethylaminopyridinium tetrafluoroborate (CDAP) chemistry.

21. The method according to claim 18 wherein the *N. meningitidis* conjugate vaccine of step b) contains conjugates wherein a ratio of MenW135 and/or MenY capsular saccharide to the tetanus toxoid carrier protein of the *N. meningitidis* conjugate vaccine of step (b) is between 1:0.5 and 1:2.

22. The method according to claim 18 wherein the *N. meningitidis* conjugate vaccine of step b) contains a MenC conjugate wherein the ratio of MenC polysaccharide to carrier protein is between 1:0.5 and 1:2.

23. The method according to claim 18 wherein the *N. meningitidis* conjugate vaccine of step (b) contains one or more *N. meningitidis* capsular saccharide(s) conjugated via a linker to the tetanus toxoid carrier protein of the *N. meningitidis* conjugate vaccine of step (b).

24. The method according to claim 23 wherein the linker is bifunctional.

25. The method according to claim 23 wherein the linker has two reactive amino groups.

26. The method according to claim 23 wherein the linker has between 4 and 12 carbon atoms.

27. The method according to claim 23 wherein the linker is adipic acid hydrazide (ADH).

28. The method according to claim 23 wherein the *N. meningitidis* capsular saccharides is conjugated to the linker with CDAP chemistry.

29. The method according to claim 23 wherein the carrier protein is conjugated to the linker using carbodiimide chemistry, optionally using 1-(3-Dimethylaminopropyl)-3-ethyl-carbodiimide (EDAC).

30. The method according to claim 23 wherein MenA comprises the one or more *N. meningitidis* capsular saccharide(s) conjugated via the linker to the tetanus toxoid carrier protein of the *N. meningitidis* conjugate vaccine of step (b).

31. The method according to claim 30 wherein the ratio of MenA polysaccharide to the tetanus toxoid carrier protein of the *N. meningitidis* conjugate vaccine of step (b) is between 1:2 and 1:5.

32. The method according to claim 23 wherein MenC comprises the one or more *N. meningitidis* capsular saccharide(s) conjugated via the linker to the tetanus toxoid carrier protein of the *N. meningitidis* conjugate vaccine of step (b).

33. The method according to claim 32 wherein the ratio of MenC polysaccharide to the tetanus toxoid carrier protein of the *N. meningitidis* conjugate vaccine of step (b) is between 1:2 and 1:5.

34. The method according to claim 32 wherein the *N. meningitidis* conjugate vaccine of step b) further comprises a *H. influenzae* b capsular saccharide conjugated to a carrier protein.

35. The method according to claim 32 wherein the *N. meningitidis* conjugate vaccine of step b) contains a *N. meningitidis* serogroup B antigen, a *N. meningitidis* serogroup B outer membrane vesicle preparation and/or a *N. meningitidis* serogroup B protein.

36. The method according to claim 1, wherein the *Neisseria meningitidis* conjugate vaccine of (b) does not comprise a *Haemophilus* influenza (Hib) saccharide conjugated to the tetanus toxoid carrier protein.

37. The method according to claim 1, wherein co-administration of the *Neisseria meningitidis* conjugate vaccine with the vaccine comprising DTPa in step (b) results in an at least 20% increase in immunogenicity against at least one of MenA, MenC, MenW135, and MenY compared to where the *Neisseria meningitidis* conjugate vaccine is administered alone, measured by Serum Bacteriocidal Assay (SBA).

38. The method according to claim 1, wherein co-administration of the *Neisseria meningitidis* conjugate vaccine with the vaccine comprising DTPa in step (b) results in an at least 30% increase in immunogenicity against at least one of MenA, MenC, MenW135, and MenY compared to where the *Neisseria meningitidis* conjugate vaccine is administered alone, measured by Serum Bacteriocidal Assay (SBA).

39. The method according to claim 1, wherein co-administration of the *Neisseria meningitidis* conjugate vaccine with the vaccine comprising DTPa in step (b) results in an at least 40% increase in immunogenicity against at least one of MenA, MenC, MenW135, and MenY compared to where the *Neisseria meningitidis* conjugate vaccine is administered alone, measured by Serum Bacteriocidal Assay (SBA).

40. A method of immunising against *Neisseria meningitidis* infection, comprising the steps of:
(a) immunising a human patient at a first age of between 0 and 6 months with a bacterial saccharide conjugate vaccine comprising bacterial saccharides each separately conjugated to tetanus toxoid carrier proteins, wherein the bacterial saccharides consist essentially of (i) a *N. meningitidis* serogroup C (MenC) capsular saccharide and a *Haemophilus* influenza (Hib) saccharide or (ii) a *N. meningitidis* serogroup C (MenC) capsular saccharide, a *N. meningitidis* serogroup Y (MenY) capsular saccharide and a *Haemophilus* influenza (Hib) saccharide, wherein the tetanus toxoid carrier protein is present at a total TT content of 5-40 idg per dose, wherein the bacterial saccharide conjugate vaccine is co-administered with a first vaccine comprising diphtheria, tetanus, and acellular pertussis antigens (DTPa); and
(b) immunising the human patient at a second age of between 13 and 20 months with a *Neisseria meningitidis* conjugate vaccine comprising *N. meningitidis* serogroup A capsular saccharide (MenA), *N. meningitidis* serogroup C capsular saccharide (MenC), *N. meningitidis* serogroup W135 capsular saccharide (MenW135), and *N. meningitidis* serogroup Y capsular saccharide (MenY) conjugated separately to a tetanus toxoid carrier protein which is present at a total dose of 30-80 µg, wherein the *Neisseria meningitidis* conjugate vaccine is co-administered with a second vaccine comprising DTPa,
wherein co-administration of the *Neisseria meningitidis* conjugate vaccine with the vaccine comprising DTPa in step b) results in an at least 10% increase in immunogenicity against at least one of MenA, MenC, MenW135, and MenY compared to where the *Neisseria meningitidis* conjugate vaccine is administered alone, measured by Serum Bacteriocidal Assay (SBA).

* * * * *

UNITED STATES PATENT AND TRADEMARK OFFICE
CERTIFICATE OF CORRECTION

PATENT NO. : 11,883,478 B2
APPLICATION NO. : 14/777985
DATED : January 30, 2024
INVENTOR(S) : Yaela Baine et al.

Page 1 of 1

It is certified that error appears in the above-identified patent and that said Letters Patent is hereby corrected as shown below:

In the Claims

Column 23, Claim 1, Line 30:
"idg per dose; and" should read: --µg per dose; and--.

Column 26, Claim 40, Lines 29-30:
"5-40 idg per dose," should read: --5-40 µg per dose,--.

Signed and Sealed this
Twenty-first Day of January, 2025

Coke Morgan Stewart
*Acting Director of the United States Patent and Trademark Office*